United States Patent [19]
Swartz et al.

[11] Patent Number: 5,706,805
[45] Date of Patent: Jan. 13, 1998

[54] APPARATUS AND METHODOLOGY FOR DETERMINING OXYGEN TENSION IN BIOLOGICAL SYSTEMS

[75] Inventors: Harold M. Swartz, Lyme; Fuminori Goda, Hanover; Tadeusz Walczak, Hanover; Ke Jian Liu, Hanover, all of N.H.; Karsten Mäder, White River Junction, Vt.

[73] Assignee: Trustees of Dartmouth College, Hanover, N.H.

[21] Appl. No.: 476,566

[22] Filed: Jun. 7, 1995

Related U.S. Application Data

[63] Continuation-in-part of Ser. No. 105,459, Aug. 12, 1993, Pat. No. 5,494,030.

[51] Int. Cl.$^6$ .......................................... A61B 5/14
[52] U.S. Cl. ........................................ 128/632; 128/653.4
[58] Field of Search ..................... 128/632, 653.2, 128/653.4, 653.5, 654; 324/316, 317; 436/173, 63

[56] References Cited

U.S. PATENT DOCUMENTS

| | | | |
|---|---|---|---|
| 4,560,663 | 12/1985 | Nicksic et al. | 324/316 |
| 4,593,248 | 6/1986 | Hyde et al. | 324/317 |
| 4,714,886 | 12/1987 | Halpern | 324/316 |
| 4,803,124 | 2/1989 | Pilbrow et al. | 324/316 |
| 5,204,628 | 4/1993 | Kunishi et al. | 324/316 |
| 5,233,303 | 8/1993 | Bales et al. | 324/316 |

OTHER PUBLICATIONS

Crepeau et al., "Communications—Composite Pulses in Time–Domain ESR", J. of Magnetic Resonance Imaging, vol. 84, pp. 184–190 (Aug. 1989).

Glockner et al., "In Vivo Oximetry Using a Nitroxide–Liposome System," J. of Magnetic Resonance, vol. 20, pp. 123–133 (Jul. 1991).

Duret et al., "Oxygen concentration measurements using the ESR line modification of PcLi molecules" Sensors and Actuators B Chemical, vol. B6, pp. 269–269 (Jan. 1992).

JD. Chapman, "Measurements of tumor hypoxia by invasive and non–invasive procedures: a review of recent clinical studies," Radiotherapy and Oncology, pp. 13–19, Suppl. 20 (1991).

Smirnov et al., "Simultaneous Multi–Site EPR Spectroscopy in Vivo," Magnetic Residence in Medicine, vol. 30, pp. 213–220 (Aug. 1993).

Swartz et al., "India Ink: a potential clinically applicable EPR oximetry probe,"Magnetic Resonance in Medicine, vol. 31, pp. 229–232 (Feb. 1994).

Swartz et al., "Measurements of Pertinent Concentrations of Oxygen in Vivo," Magnetic Resonance in Medicine, vol. 20, No. 2, pp. 333–339 (Aug. 1991).

(List continued on next page.)

*Primary Examiner*—Ruth S. Smith
*Attorney, Agent, or Firm*—Curtis A. Vock

[57] ABSTRACT

The invention provides apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1–2 GHz range. The EPR spectra is then measured at the biological system to determine oxygen concentration. The EPR spectra is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively. The paramagnetic material can be used non-invasively or invasively depending on the goals of the pO2 measurement. A detecting inductive element, as part of the EPR spectrometer resonator, is adapted relative to the measurement particularities.

11 Claims, 19 Drawing Sheets

OTHER PUBLICATIONS

K.J. Liu et al., "Lithium phthalocyanine: a probe for electron paramagnetic resonance oximetry in viable biological systems," Proceedings of the National Academy of Sciences, pp. 5438–5442, vol. 90, No. 12 (Jun. 1993).

J.M. Vanderkooi et al., "Oxygen in mammalian tissue: methods of measurement and affinities of various reactions," American Journal of Physiology, pp. C1131–C1150, vol. 260, No. 6 (Jun. 19).

James Glockner et al., "In vivo EPR oximetry using two novel probes: fusinite and lithium phthalocyanine," Oxygen Transport to Tissue XIV, pp. 229–234, Plenum Press, New York (1992).

Ernst Epstein, "Surgical Gem," The Journal of Dermatalogical Surgery and Oncology, pp. 273–274, vol. 15, No. 3 (Mar. 1989).

H.M. Swartz et al., "The use of EPR for the measurement of the concentration of oxygen in vivo tissues under physiological pertinent conditions and concentrations," The Journal of Dermatological Surgery and Oncology, pp. 221–228, vol. 15, No. 3 (Mar. 1989).

Arie H. Bartel et al., "Malignant melanoma arising at tattoo sites used for radiotherapy field marking," The British Journal of Radiology, pp. 913–914, vol. 53, No. 633 (Sep. 1980).

M. Brian Fennerty et al., "Effectiveness of India ink as a long–term colonic mucosal marker," The American Journal of Gastroenterology, pp. 79–81, vol., 87, No. 1 (Jan. 1992).

William J. Whalen et al., "Skeletal Muscle PO2 effect of inhaled and topically applied O2 and CO2," American Journal of Physiology, pp. 973–980.

Thomas E. J. Gayeski et al., "Intracellular PO2 in long axis of individual fibers in working dog gracilis muscle," The American Journal of Physiology, pp. H1179–H1186.

APPARATUS AND METHODOLOGY FOR DETERMINING OXYGEN TENSION IN BIOLOGICAL SYSTEMS

REFERENCE TO RELATED APPLICATIONS

This is a continuation-in-part of commonly-owned and U.S. patent application Ser. No. 08/105,459, filed on Aug. 12, 1993, now U.S. Pat. No. 5,494,030, and which is herein incorporated by reference.

FIELD OF THE INVENTION

This invention relates generally to apparatus and methods for determining oxygen tension in biological systems. More particularly, the invention concerns apparatus and methods for determining oxygen concentration, or $pO_2$, in biological in vivo tissue utilizing physiologically acceptable paramagnetic materials and electron paramagnetic resonance oximetry.

BACKGROUND OF THE INVENTION

Benefits derived from the measurement of oxygen concentrations in tissue are known. Oxygen is the primary biological oxidant, and the measurement of $pO_2$ can improve the evaluation and understanding of many physiological, pathological, and therapeutic processes. Specifically, $pO_2$ is an extremely important parameter in the therapy, diagnosis, and understanding of disease.

Prior art systems and methods for measuring oxygen concentrations in tissue are also known, including: the Clark electrode, fluorescence quenching, $O_2$ binding to myoglobin and hemoglobin, chemiluminescence, phosphoresence quenching, and spin label oximetry. However, these systems and methods have certain, and often acute, limitations, especially when used in vivo. They especially lack the qualities required for complete experimental and clinical use, such as sensitivity, accuracy, repeatability, and adequate spatial resolution. See J. Chapman, *Radiother. Oncol.* 20, 13 (1991) and J. M. Vanderkooi et al., "Oxygen in Mammalian Tissue: Methods of Measurement and Affinities of Various Reactions", *Am. J. Physiol.* 260, C1131 (1991).

The polarographic microelectrode is one popular device for measuring oxygen tension in tissue. However, it has obvious technical difficulties associated with the repeated insertion of the microelectrode into the tissue. For example, the microelectrode often damages the tissue, and there is repeated difficulty in re-positioning the microelectrode at the same test location. The microelectrode is also relatively insensitive to oxygen concentrations below 10 mm Hg, which is within the required sensitivity region for effective oximetry. Finally, the microelectrode may itself consume oxygen, thereby altering its own environment, inducing measurement errors, and reducing the accuracy and usefulness of the evaluation process.

There are scattered reports which concern in vivo $pO_2$ measurements with such devices, especially in skeletal muscle. Whalen and Nair, *Am. J. Physiol.* 218, 973 (1970), measured $pO_2$ of cat gracilis at rest using a recessed Au 1–5 μm microelectrode, giving average $pO_2$ values of 6.6±0.4 mm Hg (n=372). Gayeski et at., *Am. J. Physiol.* 254, H1179 (1988), measured $pO_2$ of dog gracilis at rest, exhibiting a partial pressure range of 4.5–35 mm Hg (16.8 mm Hg median), and 95% $VO_2$ max, using a Mb saturation technique, exhibiting a partial pressure range of 0.2–2.3 mm Hg (0.9–1.8 range of mean). Nevertheless, there are effective limitations to these $pO_2$ measurement techniques. In the microelectrode method, for example, it is technically difficult to monitor or make long term evaluations of $pO_2$. In the Mb saturation method, it is especially difficult to measure low $pO_2$, and the method can only be used in muscle.

Nuclear Magnetic Resonance (NMR) techniques have been explored and considered in the context of oxiometric measurements, especially through the use of an oxygen dependent proton hyperfine line in myoglobin and oxygen dependent relaxation of fluorine nuclei. NMR is a common spectroscopic technique in which the molecular nuclei is aligned in a magnetic field and simultaneously excited by absorption of radiofrequency energy. The molecular relaxation from the excited state to the initial state is an observable event that is affected by the presence of oxygen through exchange or dipolar actions. However, the NMR techniques have not demonstrated sufficient sensitivity and/or applicability to the measure of $pO_2$ in either experimental or clinical settings.

Electron Paramagnetic Resonance (EPR) oximetry is another technique for measuring oxygen concentrations. Similar to NMR, EPR oximetry is a spectroscopic technique based upon the Zeeman effect and the line-broadening effect of molecular oxygen on the EPR spectra of paramagnetic materials. These materials have unpaired electron spins that are aligned in a magnetic field and excited by microwave energy. The separation between the lower, unexcited energy state and the higher, excited energy state is proportional to the strength of the magnetic field. The presence of oxygen with the excited molecule measurably affects the molecular relaxation so that the line width of the EPR spectra changes and provides an indication of $pO_2$.

Nitroxides exemplify one family of compounds having paramagnetic quality that are suitable for EPR oximetry, and which have been used in a variety of in vitro experiments. Although nitroxides have also been tested in vivo, at least two resulting problematic areas exist in such measurements: first, nitroxides tend to be bioreduced; and secondly, nitroxides are not very sensitive to the low concentrations of oxygen that are of the most biological interest today, i.e., less than 10 Torr.

Other recent discoveries of new paramagnetic materials, such as Fusinite and lithium phthalocyanine (LiPc), have made progress as oxygen probes in the field of in vivo EPR oximetry. These two compounds, for example, are suitable for in vivo usage because they exhibit certain favorable characteristics, including: accuracy; spatial resolution; sensitivity in the physiologically important concentration range of $pO_2$; ease of use; little or no apparent toxicity; and relative stability in tissues, permitting prolonged measurements over periods of weeks or months after administering the compound. Nevertheless, because these paramagnetic compounds have not been previously tested in humans, they will have to undergo very long and extensive toxicological evaluation before they can be used clinically. This evaluation is likely to be prolonged because of other problems inherent in the compounds, such as stability and inertness, which encourage indefinite, unwanted persistence within the tissue.

There are other existing problems limiting the effectiveness of EPR oximetry, including the inability to measure EPR spectra efficiently and effectively, especially in vivo. Conventional EPR spectrometers, for example, typically utilize microwave frequencies, e.g., 9 GHz, that are strongly absorbed by tissue and water, and which reduce the useful depth penetration and measurement sensitivities within the tissue. Prior EPR spectrometers also cannot effectively measure EPR spectra from a biological system such as a live animal, because movements of the animal change the observed EPR spectra. This movement increases noise and reduces the accuracy. Finally, conventional EPR spectrometers have the resonator and the sample under test, e.g., tissue, within a common magnetic field. This constrains the EPR measurement/flexibility, being subject to physical size considerations, and potentially to the patient's dexterity.

It is accordingly an object of this invention to provide an improved EPR spectrometer and associated methodology that are free of the afore-mentioned difficulties.

It is another object of this invention to provide an improved apparatus and method that enables the direct measurement of oxygen concentration in biological systems, such as tissue.

It is a further object of the invention to provide improved methodology and apparatus for in vivo EPR oximetry.

Other objects of the invention will be apparent from the following description.

SUMMARY OF THE INVENTION

The invention attains these and other objects, according to one aspect, by providing a method for evaluating oxygen tensions in a biological system, including the steps of (1) introducing physiologically acceptable paramagnetic material to the biological system, (2) applying a magnetic field and an electromagnetic field to the biological system, and (3) determining the EPR spectra of the biological system. The paramagnetic material is of the type which has an EPR spectra responsive to the presence of oxygen, such as India ink, constituents of India ink having paramagnetic quality, carbon black, and other carbon-based material. The biological system includes in vivo and in vitro biological systems, biological tissues, cells, cell cultures, animals, and live human beings.

The paramagnetic materials of the invention include those carbonaceous materials such as India Ink, carbon black, coals, chars, and other oxygen-sensitive paramagnetic materials such as lithium phthalocyanine.

In one aspect, the invention provides a method for determining oxygen tension in a biological system, e.g., human skin tissue. Any physiologically acceptable paramagnetic material, such as India Ink, is introduced to a surface of the biological system, and the material is sealed against sources of oxygen that are outside of the biological system. The oxygen tension is thereafter determined from the electron paramagnetic resonance spectra of the material.

In accord with other aspects, the material is covered with a gas impermeable seal to keep the material air-tight to sources external to the biological system. In addition, a substantially gas impermeable grease can further be used to protect the material from external oxygen sources.

Preferably, the material forms a paramagnetic probe in the form of a flexible disc or rectangle, so that it can be easily handled and placed onto the biological system.

The invention also provides a method for determining oxygen tension in a biological system, including the steps of (1) enclosing a paramagnetic material within an inert carrier, (2) introducing the carrier to within the biological system, and (3) determining the oxygen tension of the biological system from the electron paramagnetic resonance spectra of the material within the carrier.

In this method, the inert carrier can be a needle; and, in one aspect, a removal member is connected to the needle so that it can be removed from the system. As such, the removal member extends from the needle to a position exterior to the biological system.

Preferably, the carrier is impermeable to the material, so that the biological system is protected from material toxicity. In still another aspect, the carrier can include a cylindrical disc.

The invention also provides certain apparatus, including an electron paramagnetic resonance spectrometer that measures $pO_2$ in a biological system. A magnet subsystem applyies a magnetic field of selectable strength to the biological system, while an electromagnetic oscillator selectively applyies electromagnetic radiation with a frequency between approximately 100 MHz and 5 GHz to the biological system.

The spectrometer also includes a resonator with a detecting inductive element for detecting the electron paramagnetic spectra of the biological system. An automatic frequency control section automatically retunes the resonator to the electromagnetic oscillator such that the frequency is substantially stable during any movement of the biological system. Finally, a computer is used to control the spectrometer and to determine the $pO_2$ based upon the spectra.

In accord with other aspects, the detecting inductive element is physically arranged to fit the physical characteristics of the biological system. For example, the detecting inductive element can include one of the following configurations: a surface coil; a flat surface element; and a coil for surrounding the biological system.

In yet another aspect, a spectrometer can include a paramagnetic material, and a gas impermeable layer sealing the material against a surface of the biological system.

The invention also provides for a ring-shaped resonator within the biological system. An encapsulated paramagnetic material is at the center of the ring-shaped resonator, and the information on the $pO_2$ is transmitted due to magnetic coupling between the external loop and the ring-shaped resonator. Preferably, the ring-shaped resonator includes a chemically-inert coating.

In still another aspect, a paramagnetic patch is provided for the selective determination of $pO_2$ in tissue. A paramagnetic material is contained within a cavity that is formed between a first gas impermeable layer and a gas permeable layer. A second gas impermeable layer, adjacent to the gas permeable layer, seals the cavity such that the cavity is substantially air-tight. The second gas impermeable layer is further removable from the gas permeable layer such that the gas permeable layer is sealeable to a selected surface of the tissue. Accordingly, the cavity is substantially protected against oxygen sources external to the tissue.

The invention also provides an electron paramagnetic resonance spectrometer that determines $pO_2$ in a biological system, including: a magnetic subsystem for selectively applying a magnetic field of selectable strength to the biological system; an electromagnetic oscillator for selectively applying electromagnetic radiation with a frequency between approximately 100 MHz and 5 GHz to the biological system; a resonator, including a detecting inductive element, for detecting the electron paramagnetic spectra of the biological system; a frequency control section for automatically retuning the resonator to the electromagnetic oscillator such that the frequency is substantially stable during movement of the biological system; and a computer for controlling the spectrometer and for determining the $pO_2$ based upon the spectra.

The invention thus provides several advantages. It provides for routine measurement of $pO_2$ in a patient's tissue by monitoring the responses of an oxygen-sensitive material placed in proximity to the tissue. The oxygen-sensitive material is selectively located with the patent's tissue so that the measurement may be flexibly obtained according to the needs or particularities of a given situation.

For example, the invention provides for measuring the $pO_2$ selectively, accurately, and repetitively at depths of up to 10 mm by introducing the oxygen-sensitive material directly into the tissue of interest through injection, or via an inert carrier. Alternatively, the $pO_2$ measurement can be made by placing an oxygen-sensitive material directly onto the patient's skin, and protecting the material from external sources of oxygen by a gas impermeable seal. In yet another aspect of the invention, a one time implantation of a small ring, e.g., a 3 mm thick ring with a 10 mm diameter, provides similar non-invasive $pO_2$ measurements at depths of up to about ten centimeters.

While there are a large number of medical conditions for which the measurement of the $pO_2$ in tissues is useful, there are several reasons why the invention is especially beneficial within the two pathologies of peripheral vascular disease and cancer: (1) a large number of patients have these diseases; (2) there is practical clinical value in modifying the treatment of patients afflicted with these diseases on the basis of measurements of oxygen concentration; (3) there is relative ease in measuring $pO_2$ according to the methods of the invention; and (4) other suitable methods of making comparable $pO_2$ measurements are lacking. More particularly, peripheral vascular disease of the legs is a frequent problem in the elderly and in patients with diabetes. The clinical care of these patients is difficult because of a lack of an objective method in the prior art to determine the oxygenation of the dermis, hypodermis, and muscles, i.e., the regions at risk for symptoms and/or hypoxic damage resulting from poor circulation. The patient's response to drugs or surgical procedures is also very difficult to determine, when based solely on the reports of the patient, especially relative to long term trends. The invention, however, alleviates these difficulties and enables the physician to obtain objective and routine measurements from several areas, on a repetitive basis, and without discomfort or danger to the patient. It can also monitor the effectiveness of both drug and surgical therapies in a rapid, non-subjective fashion.

The invention provides other advantages in the treatment of cancer, especially by radiation, which is critically dependent on the concentration of oxygen. This has been confirmed recently during clinical treatment of patients utilizing Clark-type microelectrodes in the measurement of $pO_2$. Despite the invasiveness of Clark-type approach, these studies have clearly indicated how valuable it is to have direct measurements of $pO_2$ in tumors. In accord with the invention, each patient with a suitable anomaly, e.g., head and neck tumors, breast cancer, skin cancers, and tumors involving lymph nodes (except for deep lying lymph nodes) has an initial evaluation of pO2 to determine whether a conventional treatment is likely to be effective. Thereafter, the $pO_2$ in the anomaly is repeatedly monitored, during therapy, to determine if the treatment is affecting the anomaly as expected. The radiation therapist utilizes this information to suitably alter the treatments in a time frame that is much faster than existing methods: currently, the physician finds out if hypoxic regions are present within the patient only after she learns that the tumor persists after several months.

These and other aspects and advantages of the invention are evident in the description which follows and in the accompanying drawings.

DETAILED DESCRIPTION OF THE INVENTION

The invention concerns apparatus, systems, and methods for determining the concentration or partial pressure of oxygen, $pO_2$, in biological systems, including in vivo or ex vivo tissue. The invention provides improvements to EPR oximetry by improving the sensitivity, accuracy, and repeatability of EPR techniques. The invention further provides an EPR spectrometer and a paramagnetic material that are physiologically compatible with in vivo measurements. This paramagnetic material is already approved for use with humans; and the material exhibits a measurable correlation between EPR spectra and oxygen tension over a clinically effective pressure, sensitivity, and resolution range. These methods, systems, and apparatus have immediate and important application to clinical and experimental problems which exist today, and can utilized in both an invasive and non-invasive manner.

The invention utilizes physiologically acceptable paramagnetic materials, and in particular carbon black, especially in the form of India ink, as new paramagnetic probes for EPR oximetry. India ink is a compound that is widely used in clinical settings, with no apparent toxicity. India ink has extensive prior use in humans as the basis for black tattoos, used for medical purposes as well as for personal decoration. It has also been widely used in surgery to trace pathways in tissues. India ink additionally exhibits the desired physical and chemical properties required for effective clinical EPR oximetry, having EPR spectra that is very sensitive to the presence of oxygen. In accord with the invention, physiologically acceptable paramagnetic materials—such as India ink, constituents of India ink, carbon black, or carbon-based material—are used to directly determine the $pO_2$ in biological systems, such as tissue.

The description below discusses the relevant properties of India ink, and the methodology and apparatus for determining $pO_2$ in vivo via EPR oximetry. Experimental results are given from tests conducted with live animals, and from tests demonstrating that oxygen dependent changes in India ink EPR spectra can be detected in humans. The latter experimental results are based upon the presence of India ink within an ornamental human tattoo, and the response of India ink EPR spectra to differing oxygen concentrations present at the tattoo.

Figure 1:
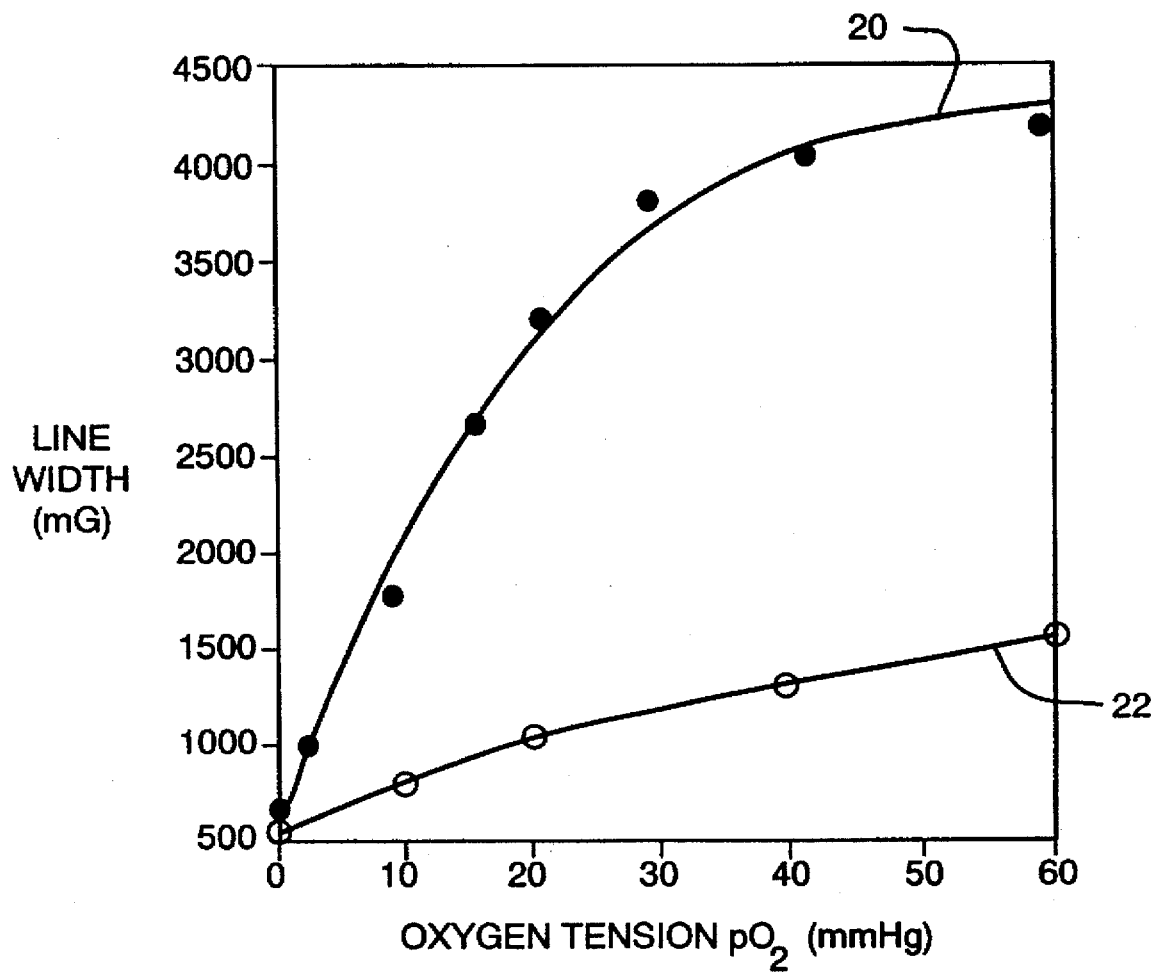
FIG. 1 graphically shows calibration EPR line width spectra of India ink and Fusinite over a wide range of oxygen tensions.

India ink is a stable paramagnetic material. It has a single EPR signal spectra with a peak-to-peak line width that is calibrated with known oxygen concentrations to directly determine $pO_2$ in vivo. FIG. 1 illustrates one set of calibration data in a graph of the EPR spectra line width of India ink 20 and Fusinite 22 against $pO_2$. With reference to FIG. 1, the India ink line width 20 is approximately 600 mGauss in the absence of oxygen and approximately 4500 mGauss in the presence of air. When India ink is within biological tissues, the shape of the EPR spectra is between these values, which is correlated to determine the in vivo concentration of oxygen. On the other hand, over the same partial pressures, the Fusinite line width only changed from 500 mGauss at 0 mm Hg to 1200 mGauss at 35 mm Hg.

At least two other noteworthy characteristics are apparent with reference to FIG. 1: first, the India Ink line width spectra is sensitive to oxygen concentrations below 1 mm Hg; and secondly, the slope of the India Ink calibration data 20 shows that the EPR spectra line width is particularly sensitive to changes in oxygen tensions of less than 30 mm Hg, which is a critical realm for effective oxiometric measurements. As compared to fusinite 22, for example, the line-broadening effects of the India ink EPR spectra per unit $pO_2$ are greater, improving sensitivity.

Figure 1A:
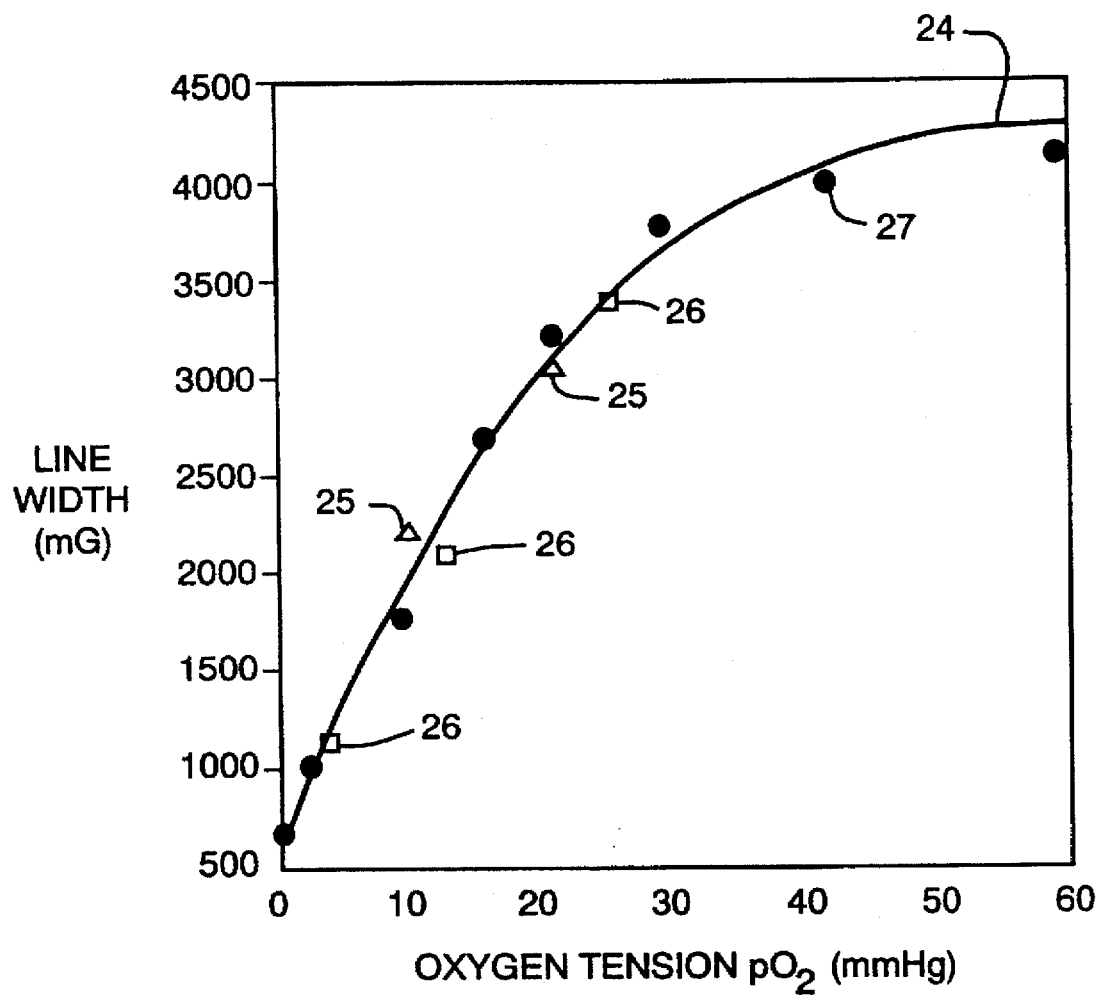
FIG. 1A graphically shows EPR line width spectra from India ink in the presence of other materials, such as water, serum and oleic acid.

India ink is additionally less sensitive to the external conditions, and to the compounds present in the biological system under investigation, which might otherwise affect or reduce measurement accuracy. Over the broad range of conditions that can occur in vivo, for example, the response of India Ink EPR spectra to $pO_2$ is essentially independent of pH, oxidants, reductants, and the nature or lipophilicity of the biological medium. FIG. 1A graphically shows the line width of India ink EPR spectra 24 in the presence of various media, including oleic acid 25, serum 26, and water 27. The data 24 is the same as the calibration data 20 of FIG. 1, to within the accuracy of the measurement.

Figure 1B:
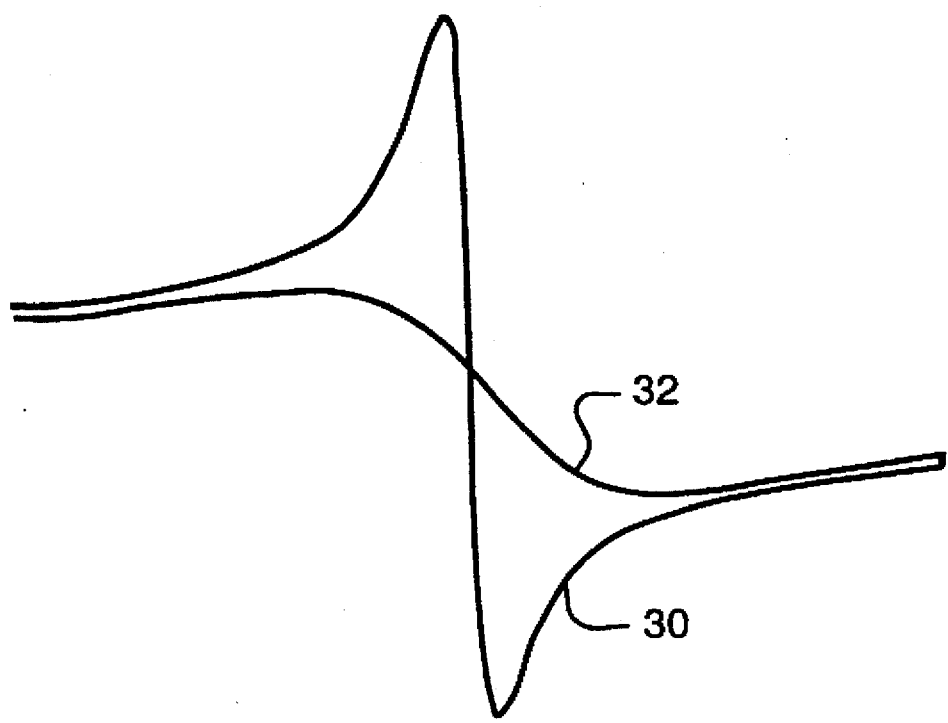
FIG. 1B graphically shows the EPR spectra of India ink in nitrogen and air using a X-band EPR spectrometer.

The experimental India ink data illustrated in FIGS. 1, 1A and 1B, and in the principal experimental data presented in FIGS. 5–8, derive from India ink purchased at SHIKAYA, JAPAN, having a concentration of 80 mg/ml. The India ink particles were homogenous in size, and were approximately 1 μm in diameter. Other chemicals for the principal experiments discussed herein were purchased from Sigma, in St. Louis, Mo.

The calibration of India ink and other in vitro experimental studies of India ink were performed on a Varian E-109 EPR spectrometer, which has an X-band, 9.6 GHz microwave oscillator. Typical control settings for the Varian spectrometer were: (1) 3210 Gauss of magnetic field strength; (2) 10 mW of microwave power; and (3) a modulation amplitude less than one third of the line width. Experimental temperatures were controlled with a Varian gas flow variable temperature control unit. And EPR spectra were collected using EW software, from Scientific Software Inc., in Normal, Ill., which was installed on an IBM - compatible personal computer. DPPH was used as a secondary standard for spin density measurements.

More particularly, the calibration of India ink was as follows. Ten micro-liters of India ink in PBS was drawn into a gas permeable Teflon tube from Zeus Industrial Products, Inc., in Raritan, N.J. This Teflon tube had a 0.623 mm inner diameter and a 0.138 wall thickness, and was folded twice and inserted into a quartz EPR tube open at both ends. The sample was then equilibrated with different $O_2:N_2$ gas mixtures. $pO_2$ in the perfusing gas was monitored and measured by a modified Clark electrode oxygen analyzer from Sensor Medics Co., Model OM-11, in Anaheim, Calif., which was calibrated with pure air and nitrogen. FIG. 1B shows that the response of the India ink EPR line width spectra 30 in air, as compared to the spectra 32 in nitrogen, is severe, indicating the ink's usefulness for oximetry.

The quantitative dependence of the EPR spectra on $pO_2$ was obtained by measuring the line width as a function of $pO_2$ in the perfusing gas. EPR line widths are usually reported as the difference in magnetic field between the maximum and minimum of the first derivative recording of the signal. In other words, the EPR line width is the peak-to-peak separation of the first derivative, with respect to frequency, of the Lorentzian-shaped absorption spectra.

Figure 2:
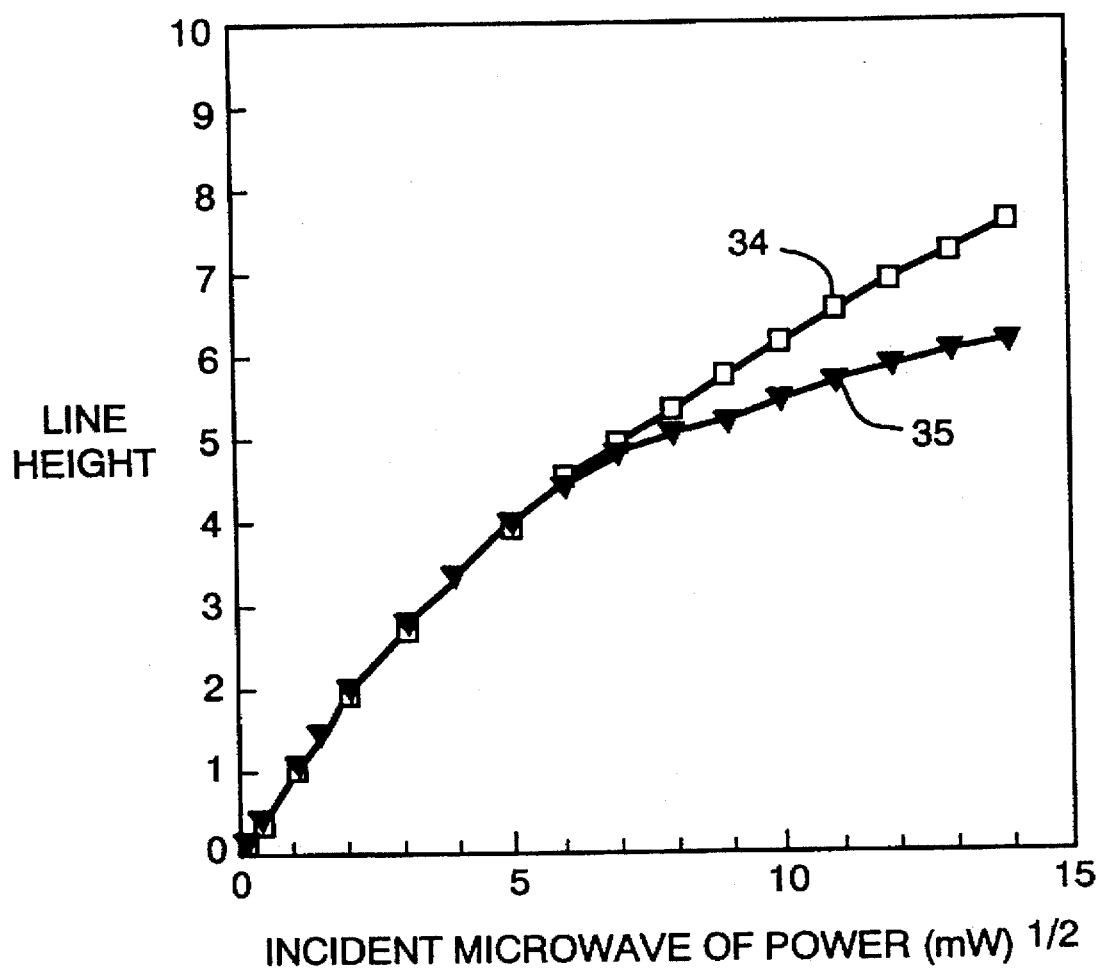
FIG. 2 graphically shows microwave power and saturation data on line height in nitrogen and in air.

The experiments presented herein also considered the microwave saturation effects of the environment. FIG. 2 summarizes microwave power data on the line height within nitrogen 34 and air 35. Because power saturation occurred only at high microwave powers, the in vitro experimental testing utilized 10 mW of unsaturated X-band microwave radiation.

With further reference to FIGS. 1 and 1A, the g-value, spin density, and line width of the EPR India ink spectra were measured at room temperature. The g-value ($2.0027 \pm 0.0008$) and spin density ($2.5 \times 10^{19}$ spin/g) of India ink were not affected by oxygen. While the g-value of India ink was approximately equal to Fusinite, the number of spins for India ink spectra was more than twice the number of spins for Fusinite ($1.0 \times 10^{19}$ spin/g). As illustrated in FIG. 1, the India ink EPR probe is very sensitive, as compared to Fusinite, at low $pO_2$, especially less than 30 mm Hg of oxygen tension. Conveniently, the principal $pO_2$ dependencies for clinical and biomedical applications occur in the range of 0–30 mm Hg $pO_2$, making India ink EPR oximetry a valuable measurement tool.

India ink EPR spectra exhibited no self-broadening due to changes in the concentration of India ink particles. No effect, for example, was observed in the EPR spectra of India ink in the presence of a paramagnetic agent, $K_3Fe(CN)_6$, an oxidant, $H_2O_2$ or a reductant, ascorbic acid. The line width of India ink was also not affected by variation in temperatures between 25° C. and 50° C., nor by variations in the pH between 4 to 14. FIG. 1A illustrates that the response of EPR India ink spectra in the presence of oxygen is essentially independent of the media, including oleic acid 25, serum 26, and water 27.

For in vivo EPR measurements, discussed below, an EPR spectrometer constructed in accordance with the further features of the invention was utilized, having a L-band, low-frequency microwave oscillator (approximately 1.2 GHz) with an extended planar loop antennae connected to a resonator.

Figure 3:
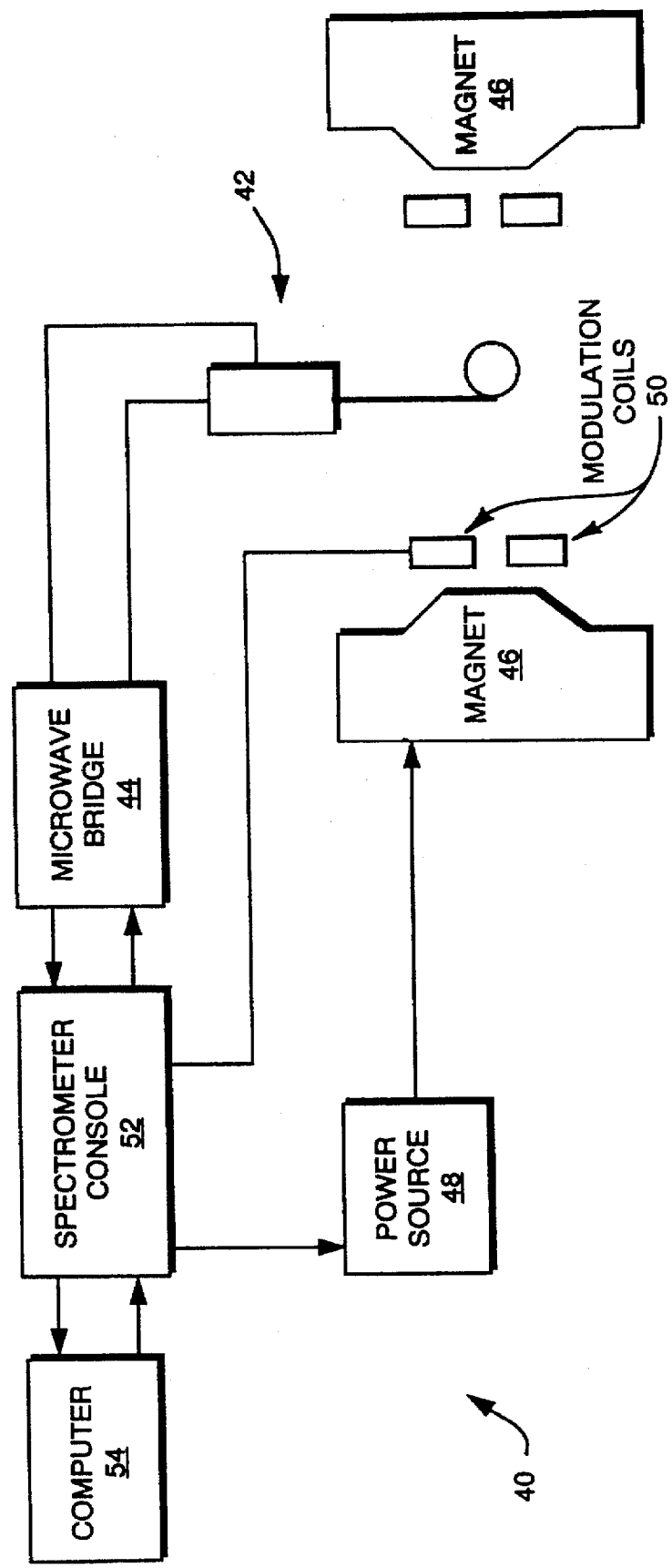
FIG. 3 is an EPR spectrometer constructed in accordance with the invention.
Figure 4:
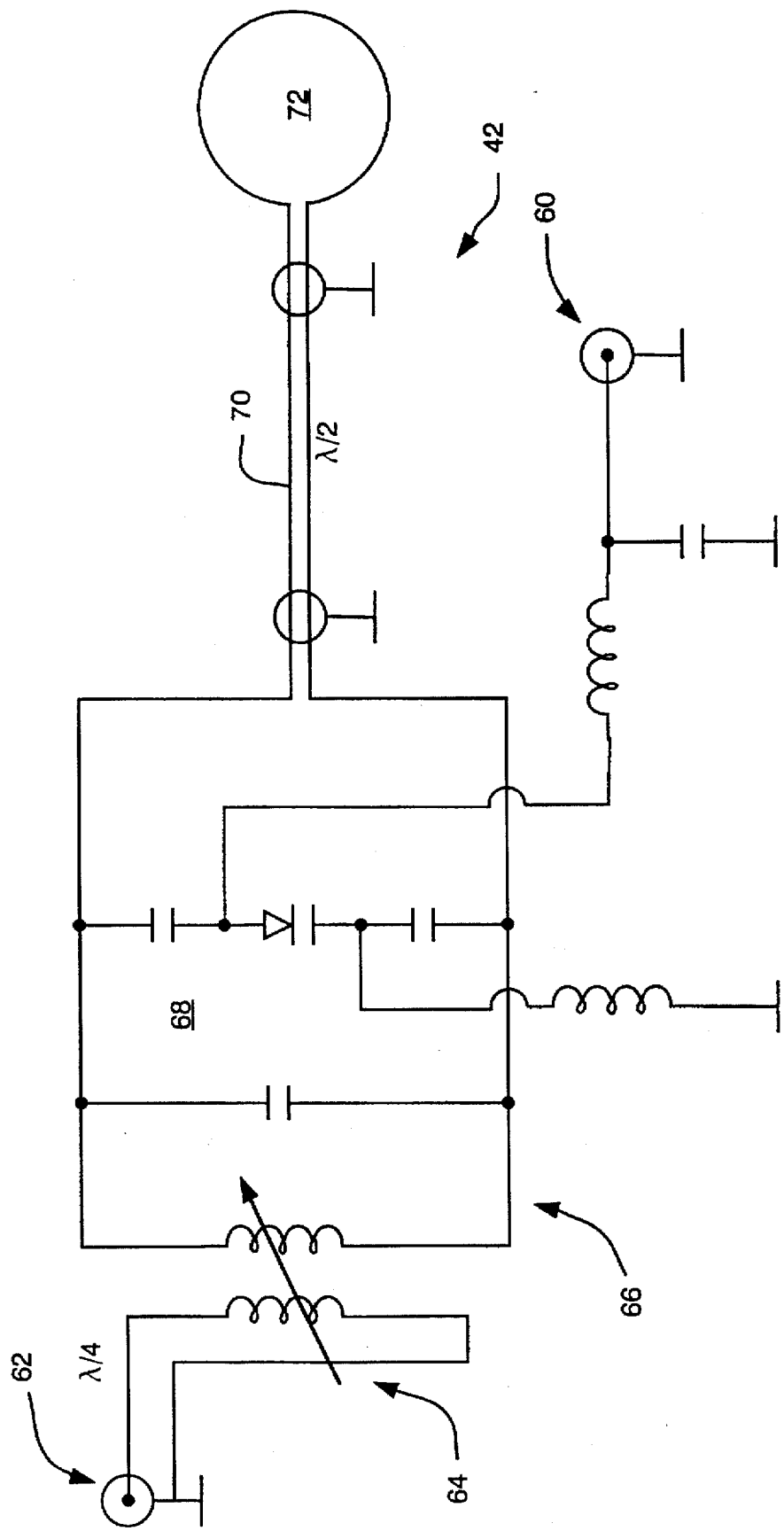
FIG. 4 is a microwave resonator for use in the EPR spectrometer of FIG. 3.

FIGS. 3 and 4 illustrate an EPR spectrometer apparatus 40 constructed in accordance with the invention, and which has significant structural differences as compared to conventional EPR spectrometers. Most significantly, the spectrometer 40 permits the accurate measurement of EPR spectra from in vivo biological systems, such as live animals, by retuning its resonator 42 to maintain resonant frequency during movements of the animal.

A spectrometer 40 constructed according to the invention solves certain technology problems which make existing EPR spectrometers incompatible with oxiometric measurements using physiologically acceptable paramagnetic materials. Existing EPR spectrometers are especially incompatible with in vivo measurements of live beings using paramagnetic probes either implanted in tissue or administered through another route, such as orally, intravenously, or by injection.

The spectrometer system 40 is a low frequency EPR spectrometer that measures the EPR spectra of India ink or other physiologically acceptable materials in animals, including humans, and other biological systems. The spectrometer 40 has a resonator 42 and an associated microwave bridge 44. The spectrometer 40 further has a magnet 46, powered by a power supply 48, and modulation coils 50. The power supply 48, the coils 50, and the microwave bridge 44 connect to a standard spectrometer console 52. A computer 54 connects to the console to control elements in the spectrometer 40.

In a conventional microwave bridge for an EPR spectrometer, an Automatic Frequency Control (AFC) circuit locks the microwave oscillator to the resonant frequency of the resonator. This is problematic for the purpose of measuring animals, or a patient, with EPR oximetry. Movements in the subject being studied cause a retuning of the oscillating bridge frequency by +/−5 MHz, which is equivalent to a shift in the position of the EPR line width by 2000 mGauss. In the spectrometer 40 of FIGS. 3 and 4, the AFC circuit has been constructed so that the resonator is tuned to the microwave source, using a varactor diode with a range of approximately +/−8 MHz. Consequently, the microwave frequency is stable and independent of movement of the experimental subject, tissue, or being under investigation.

In operation, and with reference to FIG. 3, the magnet 46 applies a magnetic field to the subject under investigation, which is adjacent to the resonator 42. This magnetic field aligns and separates spins of unpaired electrons of the subject within the field so that microwave energy is absorbed by the subject's molecules. The microwave bridge oscillator 44 and resonator 42 jointly apply a microwave electromagnetic field to the subject while maintaining a single resonant microwave frequency in the high Q resonator circuitry, illustrated in FIG. 4. The microwave energy is absorbed by the molecules according to a functional dependence with the magnetic field strength. At one magnetic field strength, the photon energy of the microwave field is matched to the excited molecular state of the electron spins, and peak absorption is attained. Other frequencies of the EPR resonance are attained by gradually changing, or "sweeping", the strength of the magnetic field generated by the magnet 46. At the other frequencies, the microwave absorption is less. A full sweep by the magnet 46 generates an absorption spectra having a Lorentzian line-shape, or, more typically, spectra presented as the first derivative of that line shape.

The presence of oxygen in a subject or tissue having a physiologically acceptable paramagnetic material, e.g., India ink, affects the relaxation rate of the excited paramagnetic molecule, thus causing an increased time-integrated intensity, or line-broadening effect within the spectra, as discussed above.

FIG. 4 illustrates the external loop resonator 42 constructed in accordance with the invention and which improves oscillator stability and sensitivity for possible resonant mismatching caused by movements of the biological tissue. The resonator 42 includes an input 60 for Automatic Frequency Control (AFC) circuitry, a high frequency input 62 for a 50 Ω coaxial line, and a variable inductive coupling 64. The resonator 42 further has a high Q LC resonant circuit 66, a varactor diode 68, a two-wire λ/2 symmetrical line 70, and a planar loop 72.

The resonator 42 avoids the physical access problems faced by conventional EPR spectrometers in co-locating the resonator and subject within a common magnetic field. The resonator 42 matches and maintains the resonant frequency of the resonator cavity by use of a high Q LC circuit 66 coupled with an external planar loop 72 via a λ/2 symmetrical line. The LC circuit 66 is matched to a 50 Ω coaxial line at the input 62 via a variable inductive coupling 64. The coupling 64 consists of a coupling loop, a λ/4 flexible impedance transformer, and a mechanism that changes the position of the loop relative to the LC circuit 66. The application of the impedance transformer makes it possible to effectively match the resonator to the 50 Ω line. The loop portion 72 is the antennae-like element which is placed in proximity to the region to be studied. The loop 72 can be configured to optimally fit the subject, e.g., by going around a protruding tumor, because the resonator need not be in the magnetic field. This is not, however, how a conventional resonator operates, where the subject and the resonator are within a common magnetic field, thereby constraining measurement flexibility.

Movement of the subject also influences the resonator's match to the 50 Ω coaxial line, which increases the high frequency voltage level at the output. This could potentially produce an overload of the preamplifier and detector, and, therefore, the spectrometer 40 of FIG. 3 preferably utilizes a wide-dynamic preamplifier and detector to measure the EPR absorption spectra.

The spectrometer 40 described in FIGS. 3 and 4 also operates at a lower frequency than conventional EPR spectrometers. Typically, conventional systems have oscillating frequencies of approximately 9 GHz, which are strongly absorbed by high dielectric materials such as water or tissue. Microwave absorption at 9 GHz operates much like a microwave oven, creating unwanted heating in clinical applications. Thus, the spectrometer 40 of FIG. 3 operates with a lower frequency microwave oscillator. One acceptable frequency range used is within L-band frequencies, i.e., 1100–1200 MHz, which provide an acceptable compromise between depth penetration and sensitivity. L-band microwave frequencies are suitable for paramagnetic probes, such as India ink, located at depths of up to ten millimeters.

However, as those skilled in the art can appreciate, the spectrometer 40 is easily constructed according to the invention at lower frequencies, such as within the radiofrequency range of 100 to 1000 MHz, to increase penetration depth while decreasing sensitivity, which may be desirable in some applications.

Those skilled in the art also understand the principal operation of the other components of the spectrometer 40, FIG. 3, and of other essential components not illustrated, as they are functionally similar to comparable, conventional EPR spectrometer components.

The advantages provided by the spectrometer 40 in the context of EPR oximetry using paramagnetic probes are several. First, the spectrometer 40 attains maximum possible depth within the target tissue while retaining sufficient sensitivity for accurate and rapid clinical and biological applications. The spectrometer 40 further is unaffected by the particular dimensions of the target tissue, or body, to be studied because the resonator 42 is not limited by the configuration of the resonant structure employed as the detector. Finally, the inevitable motions of living animals, e.g., heart beats, respiration, and small physical movements, are compensated by adjustments to the resonator frequency to maintain a balanced bridge.

Thus, the spectrometer 40 of FIG. 3 is especially well-suited for EPR measurements of animals or patients when combined with the properties of physiologically acceptable paramagnetic materials, such as India ink. This combination in accordance with the invention is suitable for many clinical and experimental uses for the direct measure of $pO_2$ in in vivo tissues.

In vivo measurements were first conducted in the gastrocnemius muscles of adult mice. A 10 µl slurry of India ink was injected into these muscles, whereafter the animals were measured for EPR spectra by an EPR spectrometer, such as the spectrometer 40 of FIG. 3. The coupled planar loop antennae 72, FIG. 4, was positioned over the area of the leg containing the India ink. When required, blood flow was restricted by a ligature around the upper leg. The animals were conscious throughout the experiment.

Figure 5:
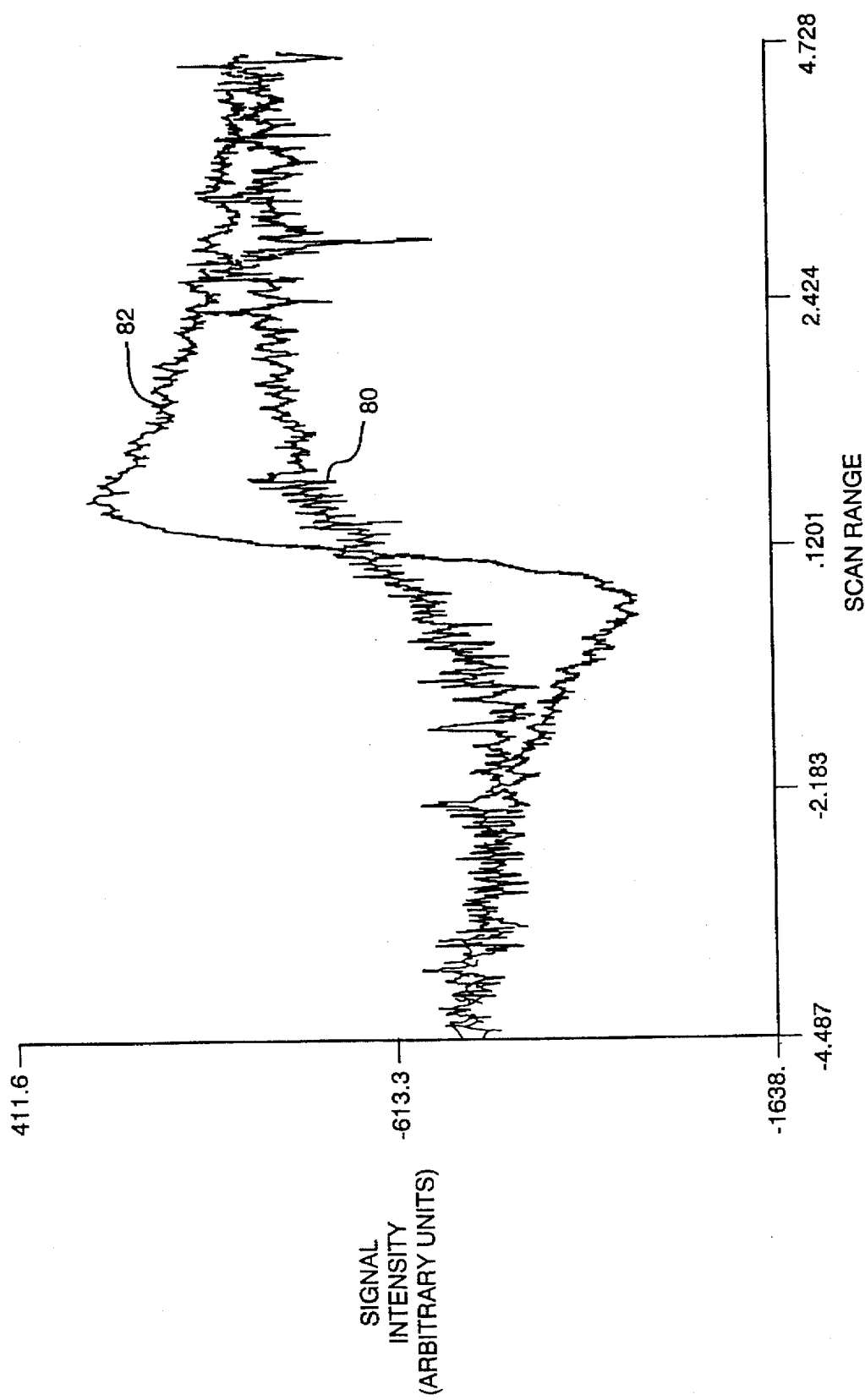
FIG. 5 shows the signal response of EPR India ink spectra before and after restricting the blood flow to the gastrocnemius muscles of an adult mouse injected with India ink.

The stability of the response of India ink EPR spectra to oxygen concentration in the mice was studied by measuring the EPR spectra before and after restricting the blood flow. FIG. 5 shows the EPR signal spectra 80 of India ink-injected gastrocnemius muscle of the mouse with unrestricted blood flow one day after implantation. When blood flow to the leg was restricted by a ligation around the upper leg, the EPR spectra response to a reduction of $pO_2$ is indicated by the narrowing line width and increased line height, as shown by the signal spectra 82. The corresponding $pO_2$ before and after the constriction of the blood flow were 11.4 mm Hg and 0.7 mm Hg, respectively.

Figure 6:
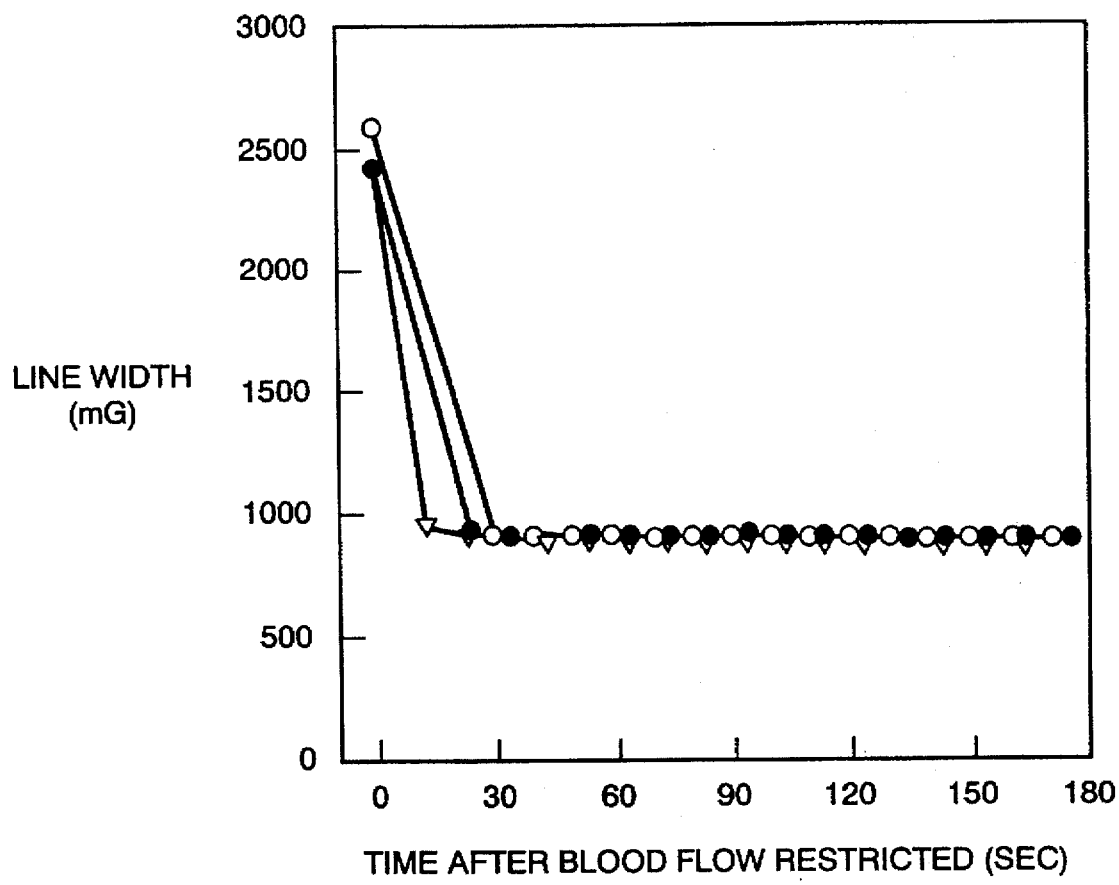
FIG. 6 graphically shows the de-oxygenation in in vivo mouse muscle injected with India ink, subsequent to the tightening of a tourniquet.
Figure 7:
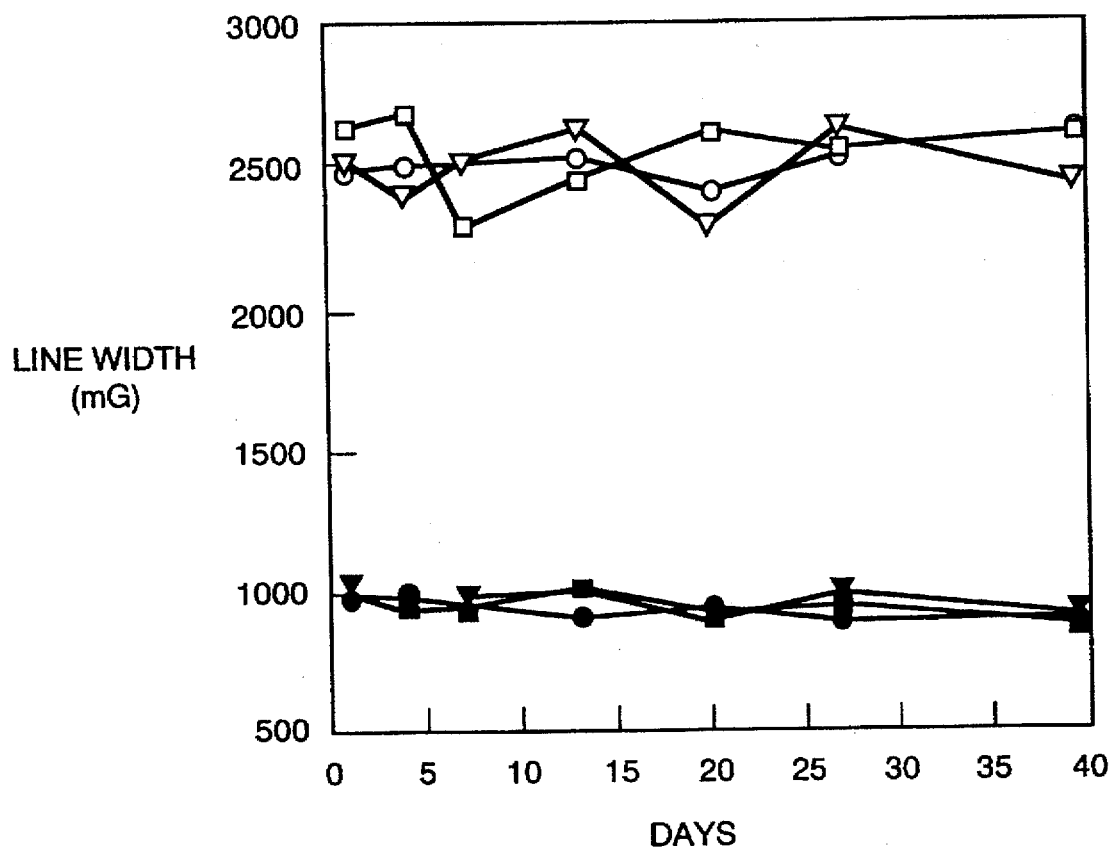
FIG. 7 graphically shows the de-oxygenation characteristics of mouse muscle injected with India ink over a period of thirty-nine days.
Figure 8:
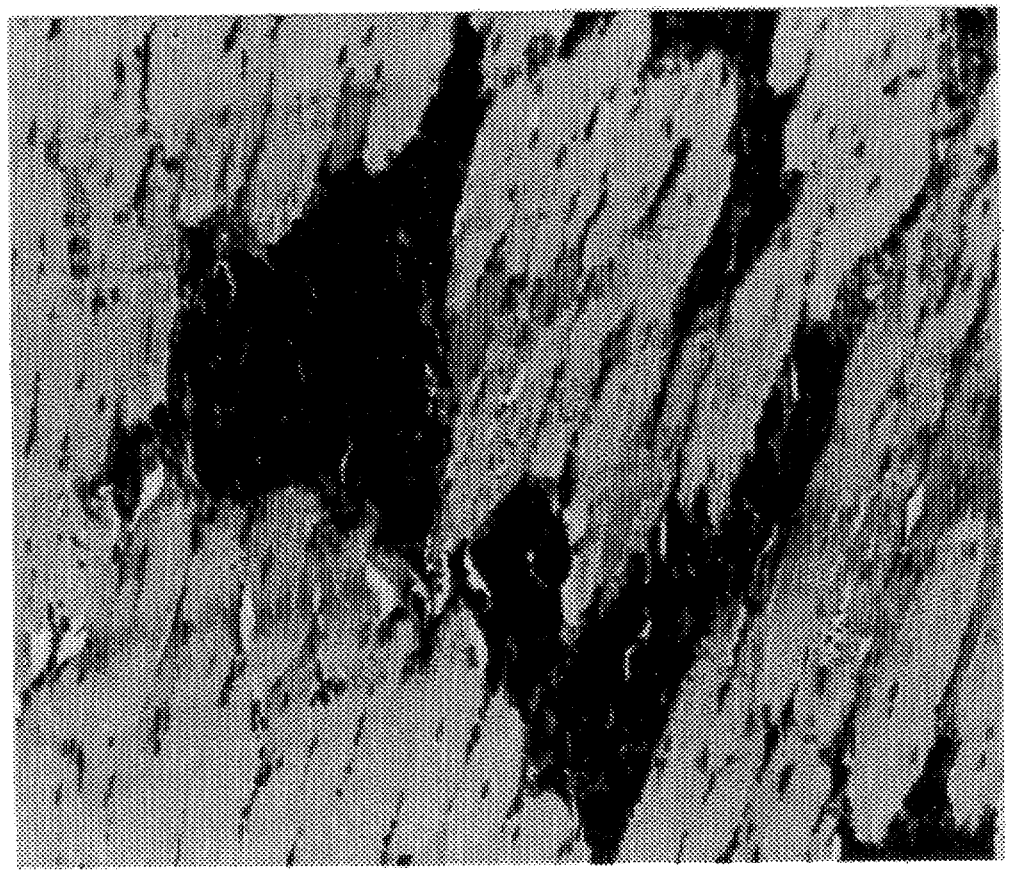
FIG. 8 shows a histological slide of mouse leg muscle forty days after implantation by India ink.

The kinetics of de-oxygenation in in vivo mouse muscle, subsequent to the tightening of the tourniquet, was also monitored. FIG. 6 graphically shows that the response of India ink is sufficiently rapid to follow the de-oxygenation, typically within 20 seconds. This response lasted for at least thirty-nine days, as shown by the periodic experimental data of FIG. 7, with little resultant toxicity, as shown in FIG. 8. The upper data points of FIGS. 6 and 7 represent unrestricted oxygen flow to the muscle; while the lower data points represent restricted oxygen flow. The multiple, co-located data points represent the several mice tested.

FIGS. 6-8 illustrate the very favorable biological properties of India ink, including stability, FIG. 7, low toxicity, FIG. 8, and the rapid response of the spectra to changes in $pO_2$, FIG. 6. Once India ink is injected into the tissue of interest, $pO_2$ is measured conveniently, rapidly, and repetitively in a non-invasive manner, i.e., through EPR oximetry. The enormous sensitivity of carbon-based materials, such as India ink, to oxygen, combined with its inert physical and chemical properties, make carbon-based physiological paramagnetic materials ideal probes for oxygen measurements in tissues, including that of animals and humans.

India ink, being clinically approved material, can immediately be used within humans to measure oxygen concentrations in clinical settings. The EPR spectrometer constructed according to the invention, e.g., the spectrometer 40 of FIG. 3, with the external loop resonator and microwave bridge, provides clinically effective EPR spectra measurement capability from paramagnetic materials in living experimental animals and human subjects. The whole process of measurement in accordance with the invention takes less than 30 seconds.

The invention offers the additional advantage of providing spatially resolved information of $pO_2$ directly, because the measured EPR spectra is detected at the specific point where the India ink is inserted. This technology is expandable, in accordance with the invention, for the simultaneous measurement of $pO_2$ at two or more test sites. A single particle of India ink can also be inserted at a selectable spatial location within the biological system or tissue to provide a selectable and spatial test probe within the system. The particle is selected according to the test biological system and can be cellular in size, e.g., 0.1 µm, or relatively large in size, e.g., one centimeter. By inserting such a particle to the system, the EPR spectra is measured from a selectable and localized region in the biological system, such as within a cell or within the liver.

Figure 9:
FIG. 9 illustrates the tattoo of a human volunteer.
Figure 10:
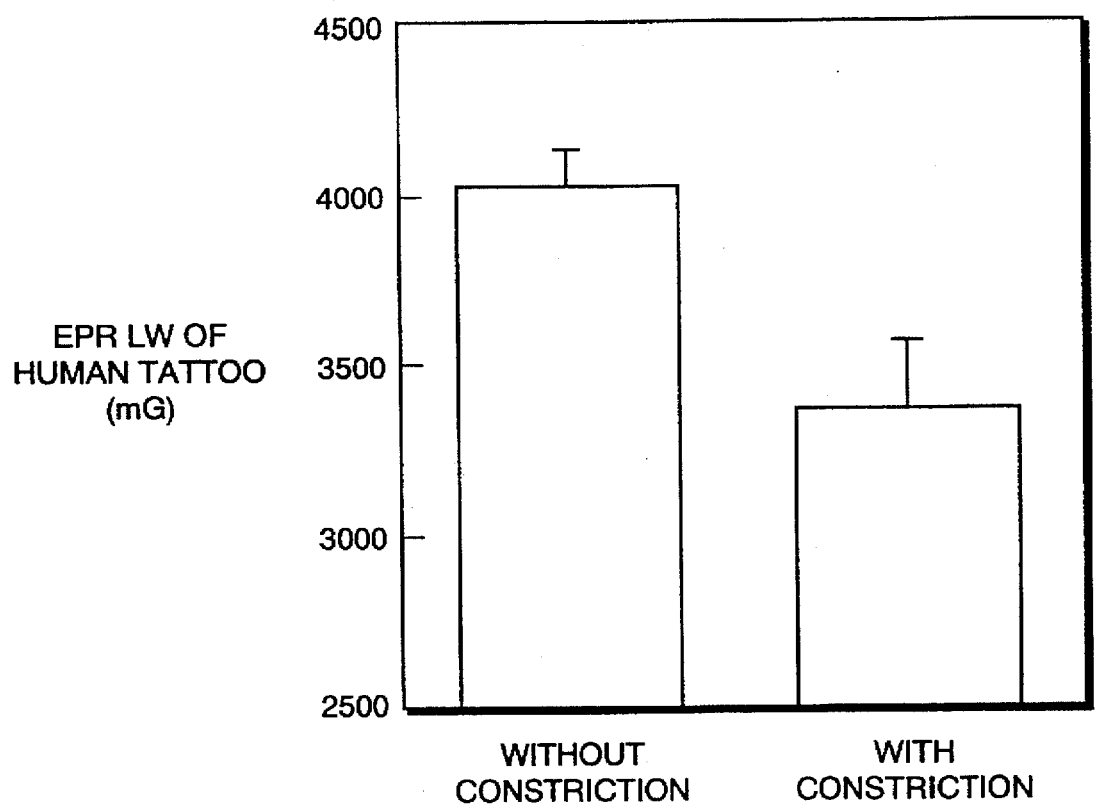
FIG. 10 graphically shows EPR spectra from a human tattoo based on India ink with and without blood flow restriction.

EPR oximetry in vivo measurements of a human subject injected with physiologically acceptable paramagnetic materials were performed through use of an extensive tattoo, illustrated in FIG. 9, comprising India ink. The human subject was a volunteer who had the tattoo on his forearm. Accordingly, the EPR spectra of the tattoo indicated the oxygenation of the skin. Similar to the experiments conducted on the mice, EPR spectra measurements were made of the tattooed skin before and after constricting the blood flow to the forearm. FIG. 10 graphically shows the India ink EPR spectra line width variation due to the constriction of the blood flow, providing a direct measurement of $pO_2$.

The particular details of the measurements in FIG. 10 are as follows. The forearm with the tattoo was placed between the poles of a magnet of an L-band microwave spectrometer constructed in accordance with the invention, such as described in FIG. 3. A prominently black area of the tattoo was positioned on the detector and spectra were obtained before and during constriction of the blood flow by means of a rubber tourniquet around the arm and above the tattoo. When the blood flow was restricted, the EPR spectra line width narrowed while its line height increased. The line width changed from 4050 mGauss, unrestricted, to 3400 mGauss, restricted.

Methods and apparatus for determining oxygen concentration in tissue having one or more of the foregoing features according to the invention have several advantages. These include the ability to directly determine oxygen concentration in in vivo tissues in order assess their state and response to therapy. This capability is especially desirable for planning, and for evaluating tumor therapy and vascular insufficiency. Furthermore, the sensitive, accurate, and repeated measurements of $pO_2$ in tissues provided for by the invention has clinical significance, especially for the optimization and utilization of cancer therapy, and for the diagnosis and treatment of vascular disease. A number of other potential clinical applications, including the evaluation of other diseases which concern oxygen pressure within tissues can also benefit from the invention by providing clinically useful information. The modern hospital may eventually utilize the teachings of the invention in an integral clinical role, especially in the oncology and cardiovascular sections of the hospital.

The invention further provides for a wide range of experimental studies that may be undertaken in small and large animals. These studies include the clinical areas described above, and may further include a wide range of studies in basic biology and physiology, because of the importance of oxygen concentrations in most physiological and pathophysiological processes. The results presented herein, particularly from the EPR studies of India ink in mice and humans, additionally indicate that methods and apparatus in accordance with the invention achieve good signal-to-noise ratios and repeatable in vivo EPR measurements, often without anesthesia. The availability and safety of the paramagnetic India ink material provide for the immediate and in vivo usage of these methods in animals and humans.

India ink has been extensively used in patients as a marker for surgical procedures and radiation therapy, in addition to its extensive non-medical use for decoration. In general surgery, India ink has been used to mark surgical resection margins. For example tattooing with India ink has been described as a precise and practical method for identifying a biopsy site when there is significant delay between biopsy and definitive surgery. E. Epstein, J. Dermatol, *Surg. Oncol.* 15, 272 (1989). India ink has also been used to indicate the location of lymph nodes and lymphatic channels. For example, Maruyama et al., *Nippon Geka Gakkai Zasshi* 901,318 (1989), injected India ink in the perigastric lymph nodes of 3,785 patients who had stomach cancer at the operation in order to find metastatic lymph nodes and reported that this technique made it easier to find lymph nodes, thereby improving prognoses. In radiation therapy, India ink is routinely used to mark fields for irradiation. For example, S. J. Walker, *Radiography Today* 54, 617 (1988), made a survey of methods for marking fields in twelve radiotherapy centers in Britain, and reported that tattooing with India ink was a standard procedure in most departments. There was no suggestion of any serious problems in tattooing. In the endoscopic field, India ink is used as a long-term colonic mucosal marker. Fennerty et al., *The American Journal of Gastroenterology* 87, 79 (1992), implanted India ink tattoos to colorectal polygas of patients who were followed for at least six months, and reported no side effects or complications.

The basis for the apparent lack of toxicity of India Ink is fairly straight-forward. India ink consists of a suspending vehicle, an emulsifier, and the "active ingredient", which is carbon black. From analyses of its physical properties, and from experience in animals and patients, the carbon black appears to be both non-reactive and non-allergenic. The particles of India ink are also very small, homogenous, and independent from each other. When the ink is injected intravenously, the particles are trapped by the reticuloendothelial system, i.e., the liver and spleen, and not in the capillaries of the lung. In vitro experiments have shown that India ink is easily taken into cells via phagocytosis, without showing any toxicity, as measured by the colony-forming ability and exclusion of trypan blue. Therefore, in accordance with the invention, India ink is also useful for the selective measurement of intracellular $pO_2$.

Figure 11:
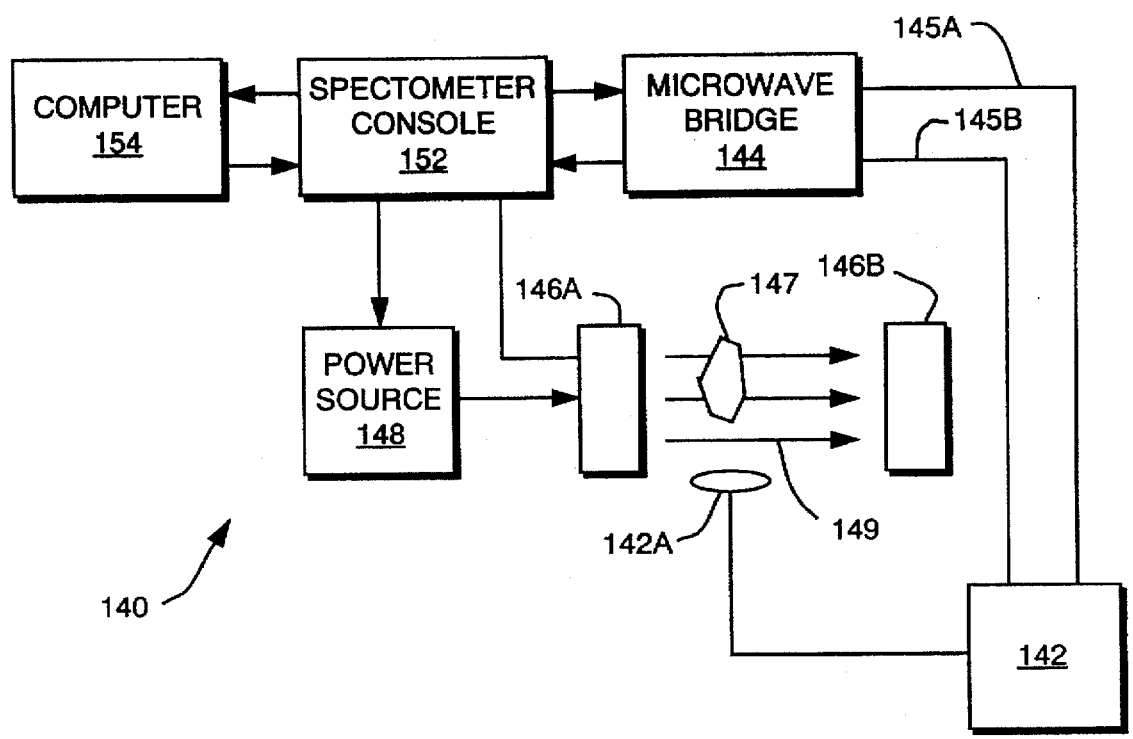
FIG. 11 is another embodiment of an EPR spectrometer constructed in accordance with the invention.

FIG. 11 illustrates an EPR spectrometer apparatus 140 constructed in accordance with the invention, similar to the spectrometer apparatus 40 of FIG. 3, and which has significant structural differences as compared to conventional EPR spectrometers. For example, the spectrometer 140 permits the accurate measurement of EPR spectra from in vivo biological systems, such as live animals, by retuning its resonator 142 to maintain resonant frequency during movements of the animal. The spectrometer apparatus 140 is particularly advantageous over prior art EPR spectrometers in that the configuration of the resonator 142 permits accurate and non-invasive measurements of pO2 in patients, such as described in more detail below.

A spectrometer 140 constructed according to the invention solves certain technology problems which make existing EPR spectrometers incompatible with oxiometric measurements using physiologically acceptable oxygen-sensitive materials, such as the paramagnetic materials of carbon black, and especially India Ink. Existing EPR spectrometers are especially incompatible with in vivo measurements of live beings using paramagnetic probes that are either implanted in tissue or administered through another route, such as orally, intravenously, or by injection. The prior art EPR spectrometers are particularly incompatible with measurements of $pO_2$ utilizing a non-invasive paramagnetic probe, such as described below.

The spectrometer system 140 is a low frequency EPR spectrometer that measures the EPR spectra of India ink or other physiologically acceptable materials in animals, including humans, and other biological systems. The spectrometer 140 has a resonator 142 and an associated microwave bridge 144, which detects imbalances in the signal from the resonator 142. The spectrometer 140 further has a power supply 148 coupled to a low intensity magnet 146A, 146B, e.g., an electromagnet, or a permanent magnet coupled to a helmholz coil, such as known to those in the art. The power supply 148 and the microwave bridge 144 connect to a standard spectrometer console 152. A computer 154 connects to the console 152 to control the several elements in the spectrometer 140, and preferably provides an output that is expressed directly as $pO_2$.

In a preferred embodiment of the invention, the resonator 142 includes an AFC circuit which automatically tunes the resonator 142 to the oscillating microwave energy generated by the bridge 144. Consequently, the microwave frequency is stable and independent of movement of the experimental subject, tissue, or being under investigation.

In operation, and with reference to FIG. 11, the magnet 146A, 146B applies a magnetic field 149 to the subject 147 under investigation, which is adjacent to the resonator 142. More particularly, the subject 147 is adjacent to the external loop, i.e., the detecting inductive element 142A of the resonator 142. The detecting inductive element 142A is similar to the loop 72 of FIG. 4, except that it is specially configured to measure $pO_2$ according to the particularities of the measurement, such as described in more detail below.

The magnetic field 149 generated by the magnet 146A, 146B aligns and separates the spins of unpaired electrons of the subject 147 within the field 149 so that microwave energy is absorbed by the subject's molecules. The microwave bridge oscillator 144 and resonator 142 jointly apply a microwave electromagnetic field to the subject while maintaining a single resonant microwave frequency in a high Q resonator circuitry, such as illustrated in FIG. 4. The microwave energy is absorbed by the molecules according to a functional dependence with the magnetic field strength. At one magnetic field strength, the photon energy of the microwave field is matched to the excited molecular state of the electron spins, and peak absorption is attained. Other frequencies of the EPR resonance are attained by gradually changing, or "sweeping", the strength of the magnetic field generated by the magnet 146A, 146B. At the other frequencies, the microwave absorption is less. A full sweep by the magnet 146 generates an absorption spectra having a Lorentzian line-shape, or, more typically, spectra presented as the first derivative of that line shape.

The magnetic field strength is modulated by techniques known in the art. For example, the magnet 146A, 146B can be an electromagnet which generates a magnetic field with a strength functionally related to the current within the electromagnetic coil. Alternatively, the magnet 146A, 146B can be a permanent magnet that is coupled with a helmholz coil (not shown), to selectively modify the strength of the field 149.

In a preferred embodiment, the resonator 142 is connected to the bridge 144 via a pair of flexible 50 Ω coaxial cables 145A, 145B. Further operating and electrical detail of the resonator 142 may be found with reference to the descriptions and illustrations of FIGS. 3 and 4.

The resonator 142 further has a detecting inductive element 142A that is configured according to the needs or particularities of the $pO_2$ measurement. In particularly, the detecting inductive element can be one of several configurations, including: (1) a surface coil type, such as shown in FIG. 4 as external loop 72, which is placed on or near to the surface of the area to be measured; (2) a flat surface element, which is particularly suited for surface measurements or deep tissue measurement; and (3) a coil that fits around the region to be measured. For example, if the region were a human finger, the configuration of (3) is preferred so that the detecting inductive element 142A can surround the finger to obtain a better signal measurement.

FIGS. 12–16A illustrate several exemplary measurement procedures, according to the invention, with differing detecting inductive elements. For illustration purposes, FIGS. 12–16A show only the tissue, paramagnetic probe configuration and detecting inductive element; and they specifically do not show the further details of the spectrometer generating and controlling the electromagnetic fields at the tissue.

Figure 12:
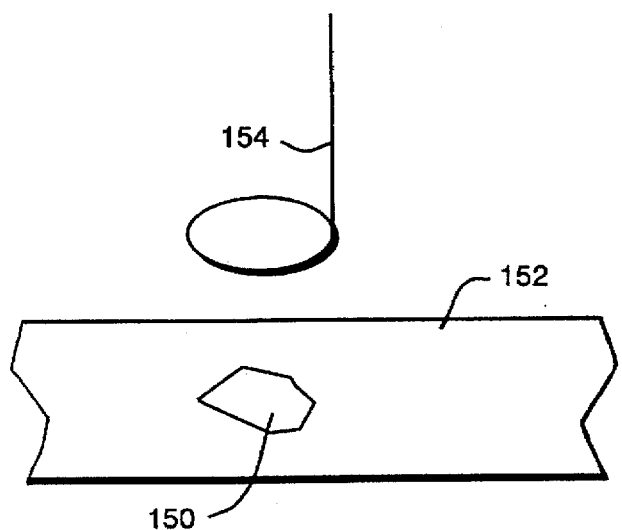
FIGS. 12–16A illustrate several methods, according to the invention, for measuring $pO_2$ in tissue, and further illustrate procedures for making the measurement invasively and non-invasively.

FIG. 12 illustrates a procedure wherein the oxygen-sensitive paramagnetic material 150 of the invention, usually India ink, is placed aseptically into the regions of interest within the tissue 152, typically by injection through a small sized hypodermic needle. The detecting inductive element 154, similar to the inductive element 142A of FIG. 11, is a loop configuration that detects signals from within the tissue 152. Multiple injections of the material 150 can be made if multiple sites are to be monitored. The position of the oxygen sensitive material 150 can be confirmed through magnetic resonance imaging. Once the material has been placed, it can be used indefinitely and no further placements are needed. The paramagnetic material such as India Ink is inert, and can therefore remain in the tissue indefinitely, as demonstrated through the widespread use of permanent markers in tissues based on India ink.

In operation, the tissue 152 of the patient is positioned appropriately in the low magnitude magnetic field 149, FIG. 11, and the detecting loop 154 is placed appropriately on the tissue 152. The measurement can be made within approximately 0.5 to 5 minutes. If multiple sites are to be measured, a magnetic field gradient also is applied to the tissue 152.

Figure 13:
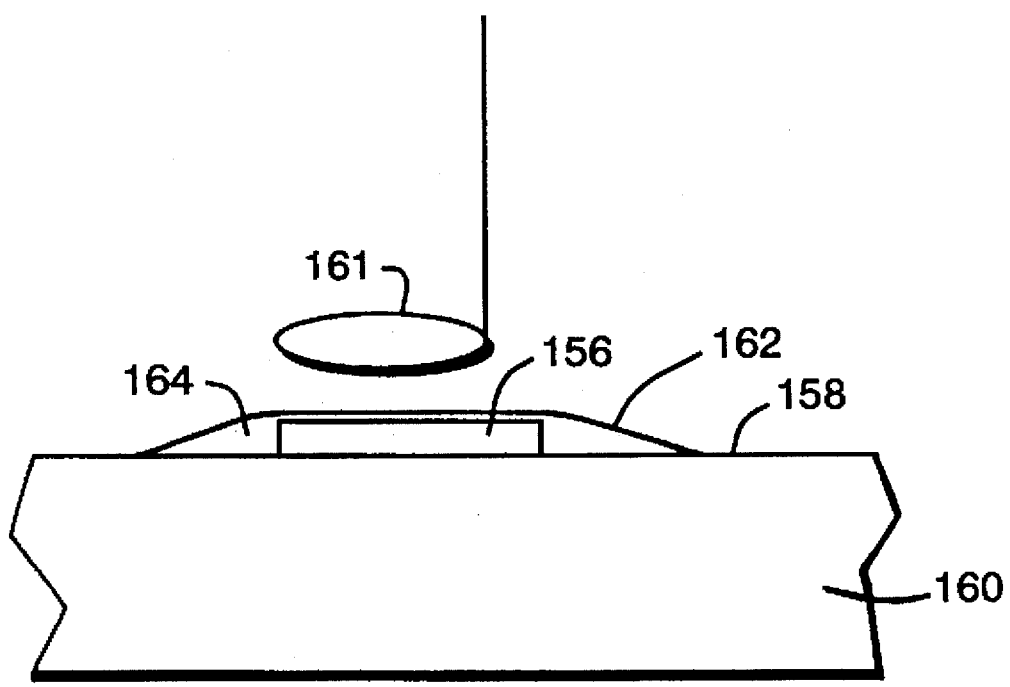

FIG. 13 illustrates an approach which differs from FIG. 12 in that the oxygen sensitive paramagnetic material 156 is placed onto the surface 158 of the patient's skin tissue 160, rather than into the tissue 160. The material 156 is covered by a gas impermeable seal 162, which can be formed of a Band-Aid like material, to shield the material from external sources of oxygen. Preferably, a sealing grease 164 further shields the material 156 from oxygen that is outside of the tissue 160. In such a configuration, the material 156 responds to the $pO_2$ of the tissue 160 over which it is placed when subjected to the electromagnetic forces of the spectrometer, e.g., the spectrometer 140 of FIG. 11.

FIG. 13 also illustrates a detecting inductive element 161 which is similar to the inductive element 142A of FIG. 11, and which is configured as a flat surface element. Such an element 161 is particularly suitable for detecting signals from the surface 158 of the tissue 160. However, it is also capable of detecting signals from deep within the tissue 160.

Preferably, the material 156 is a paramagnetic probe that forms a flexible disc or rectangle, which can be easily and selectively placed onto the tissue 160.

The advantages of the configuration illustrated in FIG. 13 are several. First, $pO_2$ is measured in an entirely non-invasive manner. Secondly, because the oxygen sensing material 152 is at the surface 158, it is very close to the detecting inductive element 162; and therefore the intensity of the signal from the paramagnetic probe 156 is very high. Third, because the material 156 does not enter the body, it is non-toxic, and there is no possibility of either short-term or long term effects because the material 156 does not get absorbed.

Figure 13A:
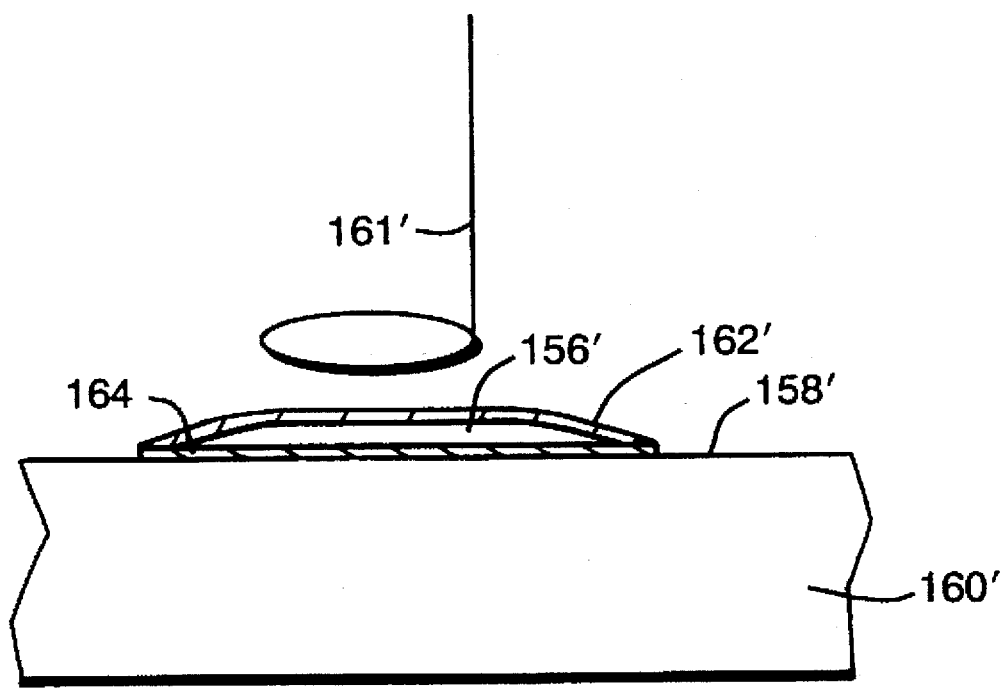

In addition, because the material 156 is not placed into the tissue 160, practically any appropriate paramagnetic material can be used without the necessity of testing, permitting the use of more sensitive paramagnetic materials, and increasing signal sensitivity. FIG. 13A shows a configuration similar to the configuration of FIG. 13, except that a gas permeable seal 164 separates a liquid paramagnetic material 156' from the tissue 160', and the sealing grease is removed (because the liquid material 156' fills the cavity between the seals 162' and 164). The seal 164 protects the patient from any unwanted contact with the material 156' selected for measurement. In particular, although India ink is already readily used in human subjects, it is not entirely adequate for certain uses, and it is not as sensitive to oxygen as some of the other materials available. The procedure illustrated in FIG. 13, and particularly in FIG. 13A, should be safe for use on infants, babies, and pregnant women, as well as on patients of all other ages and types; and there should be no illnesses which prevent its use, as long as the material is placed on unbroken skin (with the seal 164 of FIG. 13A, even this latter restriction may be disregarded).

Figure 14:
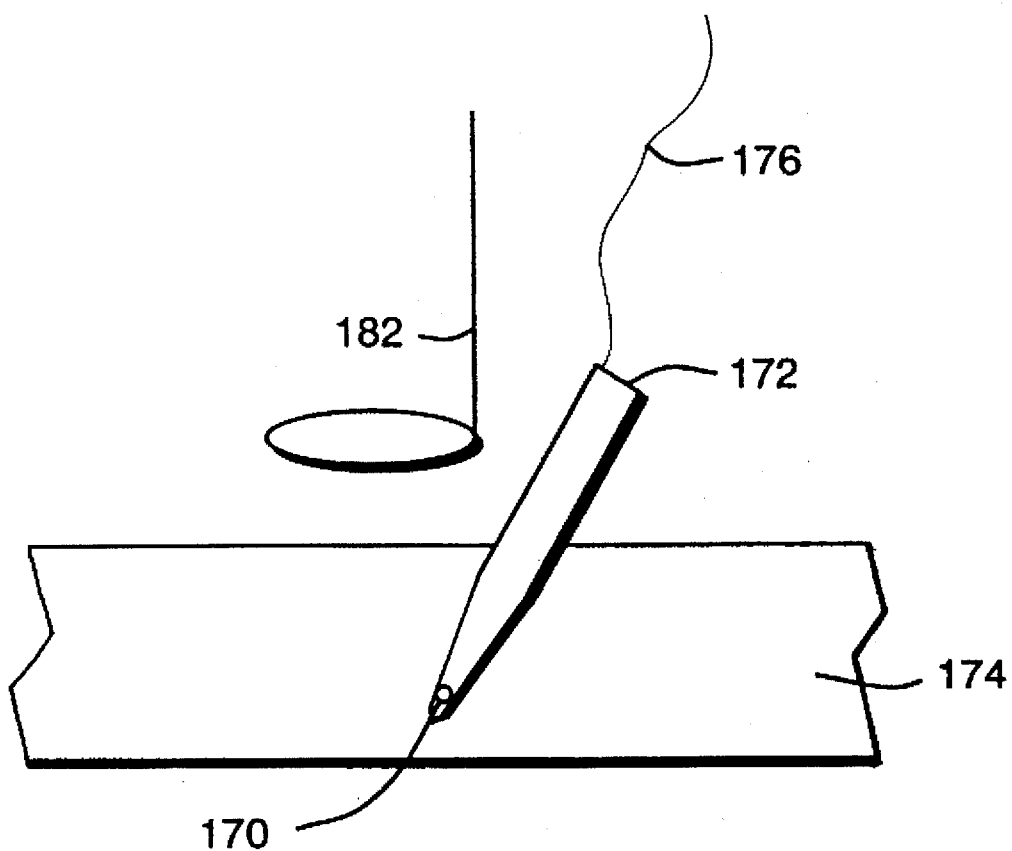

FIG. 14 illustrates a procedure whereby the oxygen-sensitive material 170 is placed in a gas-permeable inert carrier 172, which has the size of a very small needle, and which is placed into the tissue 174 at a site of interest. A removal member 176, e.g. a suture thread, rests at or near the surface 178 to facilitate later removal of the carrier 172. Unlike the procedure illustrated in FIG. 12, the material 170 is removable when there no longer is a need for the measurement of the $pO_2$ in the tissue 180, simply by pulling on the thread or the end of the thin plastic tube 172. As above, a detecting inductive element 182 hovers near to the material 170, and can be in contact with the tissue 174.

The procedure of FIG. 14 has certain advantages. Typical oxygen-sensitive paramagnetic materials are insoluble solids. The holding structure 172 can be constructed so that the paramagnetic material does not come in direct contact with the tissue 174. Therefore, the approach of FIG. 14 permits the use of any paramagnetic material, e.g., LiPc, with the appropriate $pO_2$ response, and without concern for potential toxic effects. As noted above, this can enhance the sensitivity and accuracy of the given measurement.

Figure 15:
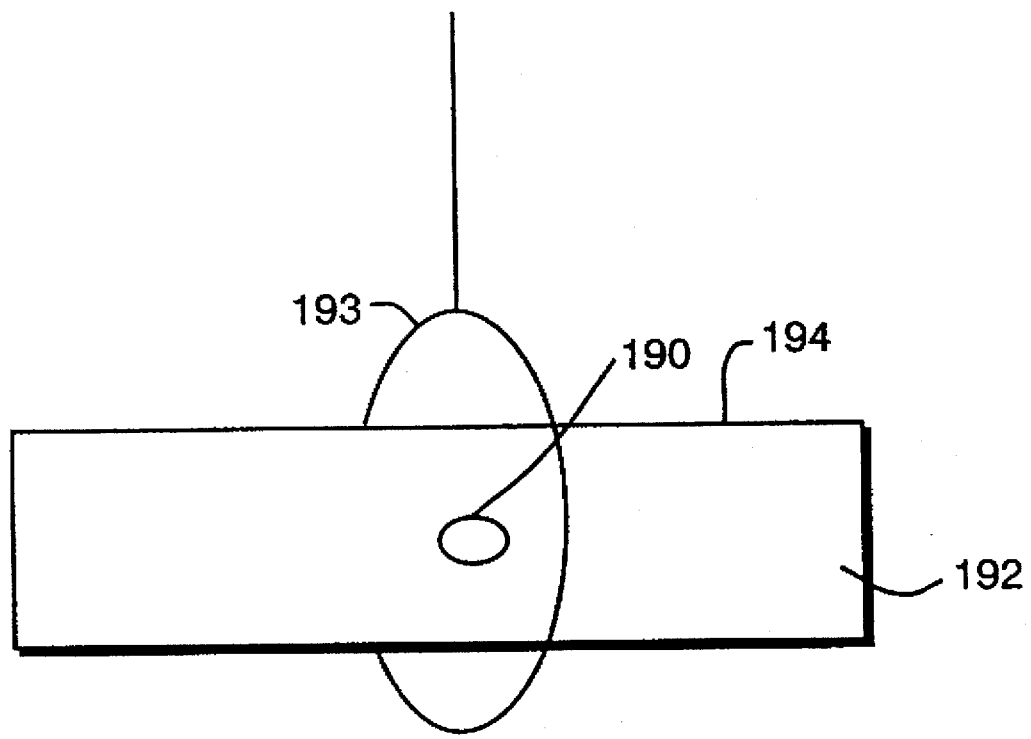

FIG. 15 illustrates a procedure of the invention whereby oxygen sensitive material is contained within a small, e.g., 0.1 mm diameter, inert cylinder or disc 190 that is placed directly in the regions of the tissue 192 to be measured. The disc 190, and hence the paramagnetic material, remains in the tissue without being connected to the surface 194. When their no longer is a need for the measurements of oxygen, the container 190 with the oxygen-sensitive material is removed through a small surgical incision. The material 190 is opaque to x-rays, and can thus be readily located.

FIG. 15 also illustrates a detecting inductive element 193 that coils around the target tissue 192, thereby providing better signal recovery and measurement accuracy.

Figure 16A:
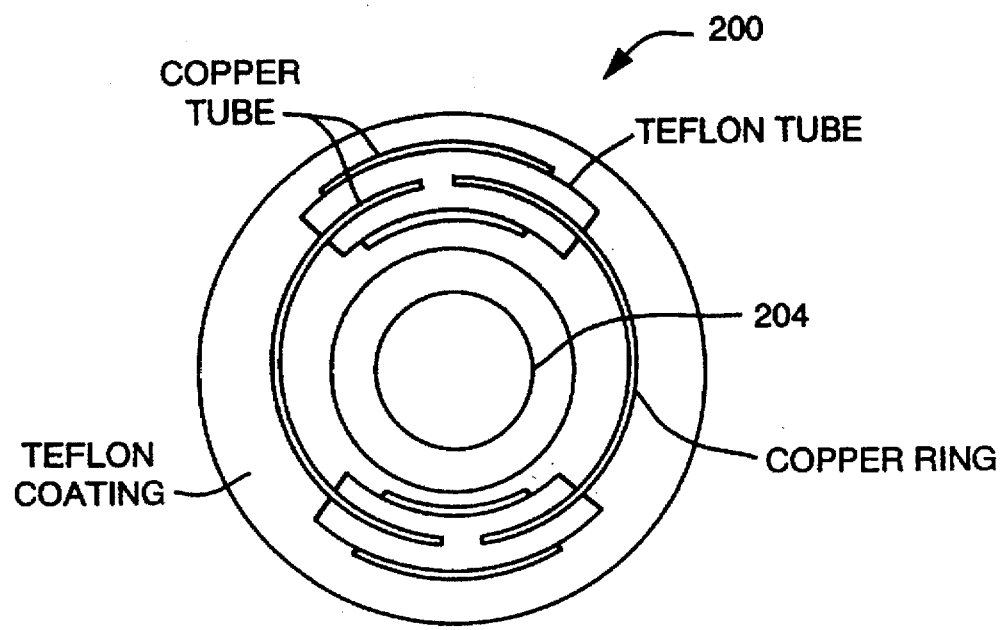
Figure 16:
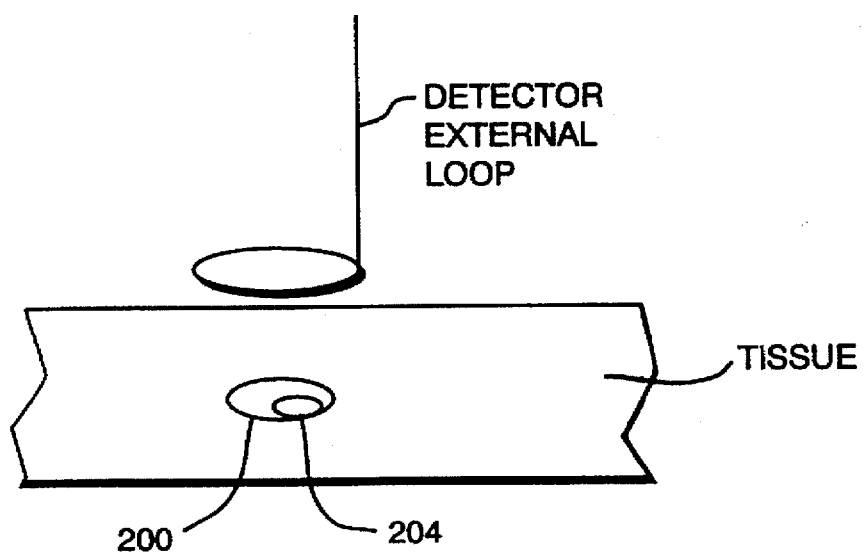

FIG. 16 illustrates one embodiment of the invention wherein a small ring-shaped resonator 200, shown in FIG. 16A, is implanted within tissue 202. In one embodiment, the dimensions of the resonator 200 are approximately 10 mm in diameter and 4 mm thick. Other acceptable configurations include 8–10 mm diameters, and 2–4 mm thicknesses. The ring 200 is coated with a layer of Teflon or another material that is chemically inert, providing good electrical insulation from the surrounding tissue 202. The encapsulated paramagnetic material 204 is placed at the center of the ring 200. The measurement principle illustrated in FIG. 16A is based upon a magnetic coupling between the external loop, e.g., the detecting inductive element of the resonator 142, FIG. 11, and the implantable resonator 200. No physical connection between them is required. While this approach is invasive, it has the advantage of extending the usable range of pO$_2$ measurements by a factor of up to ten, thereby making deep lying structures amenable for measurements.

The resonator 200 can also be placed within a needle or catheter. For example, and with reference to FIG. 14, the resonator 200 can be positioned like material 170 within a needle or catheter 172.

The advantages provided by the spectrometer 140, FIG. 11, in the context of EPR oximetry using paramagnetic probes are several. First, the spectrometer 140 attains useful depth within the target tissue 147 while retaining sufficient sensitivity for accurate and rapid clinical and biological applications. The spectrometer 140 further is unaffected by the particular dimensions of the target tissue, or body, to be studied because the resonator 142 is not limited by the configuration of the resonant structure employed as the detecting inductive element 142A. Finally, the inevitable motions of living animals, e.g., heart beats, respiration, and small physical movements, are compensated by adjustments to the resonator frequency to maintain a balanced bridge.

Thus, the spectrometer 140 is especially well-suited for EPR measurements of animals or patients when combined with the properties of physiologically acceptable paramagnetic materials, such as India ink. This combination in accordance with the invention is suitable for many clinical and experimental uses for the direct measure of pO$_2$ in in vivo tissues in either an invasive or non-invasive manner.

Figure 17:
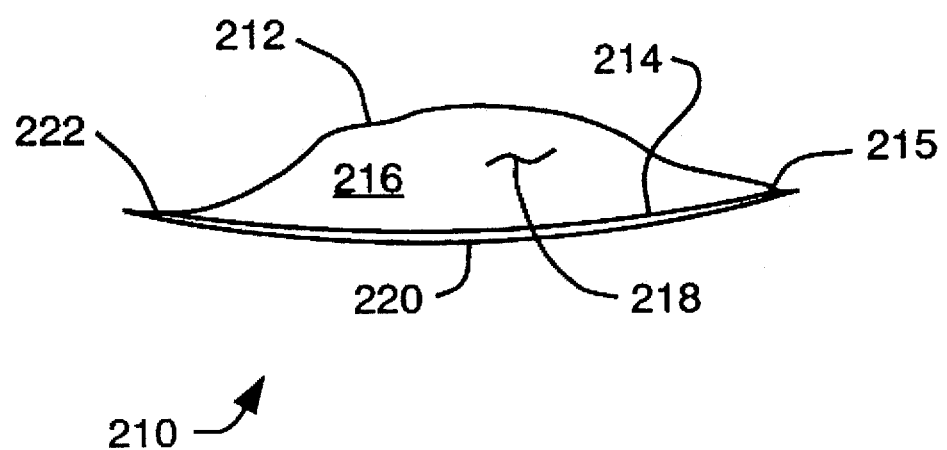
FIG. 17 shows a self-contained paramagnetic patch, constructed according to the invention, that enables $pO_2$ measuement at a selective location on a patient's tissue.

FIG. 17 illustrates a paramagnetic patch 210 constructed according to the invention. The patch 210 includes a first gas impermeable layer 212, and a gas permeable layer 214. The layers 212, 214 are sealed together along their perimeter 215 such that a cavity 216 is formed therebetween. A paramagnetic material 218, such as described herein, fills the cavity 216; and a second gas impermeable layer 220 seals the cavity into an air-tight configuration.

In use, the second gas impermeable layer 220 is removed, e.g., peeled off, and the patch 210 is sealed to the tissue of interest and along the gas permeable layer 214. Once connected to the patient's tissue, the configuration of the patch operates like the material 156', layer 162' and seal 164 of FIG. 13A to determine pO$_2$.

Preferably, the patch 210 includes a perimeter seal 222 that becomes exposed once the layer 220 is removed. The perimeter seal 222 has a medically-accepted glue that seals the patch directly to the tissue of interest.

Those skilled in the art will appreciate that variations of the above techniques, and of the spectrometer instrument, can be developed for intraoperative use and/or for use with an insertion apparatus. By way of example, an inductive element incorporated with a catheter can be used to measure very deep tissue structures that are injected with paramagnetic material. Alternatively, the catheter can be externally coated with an oxygen-sensitive paramagnetic material to make measurements of pO$_2$ proximal to the catheter, such as within an artery.

Further, there are additional applications of the invention in the study of parameters other than pO$_2$. These include the capability of detecting and characterizing free radical intermediates, which are considered to be very important components of the wide range of diseases, and treatments that involve "oxygen radicals" or "free radical pathology". Another set of likely widespread clinical uses of the invention will take advantage of the ability of in vivo EPR spectroscopy to study pharmacokinetics, using spin labels in ways that are analogous to radioactive labels, but with two very important additional advantages: first, they do not involve the use of radioactive materials; and secondly, the spin labels can provide additional data on the environment in which the drug/tagged material is located, including information on pH, molecular motion, differential tissue distribution, release of drugs from polymers or other sustained release systems, and the state of drug delivery systems such as liposomes.

There are still other uses of the invention, as should be apparent to those skilled in the art. Such uses can be illustrated by further reference to FIG. 12. If, for example, the material 150 were replaced with a pH-sensitive nitroxide, in vivo measurements of pH can be made with the spectrometer described herein. A spectra corresponding to pH is determined in a manner similar to the pO$_2$ spectra described above. A measurement of temperature can also be made by monitoring the temperature-dependent changes in the EPR spectra.

A measurement of perfusion can also be made by the invention by monitoring the wash-out of paramagnetic materials injected into the site of interest. For example, a measurement of tissue perfusion in tissue 152 can be made by observing the wash-out of material 150 over time.

Thus, the invention be used to monitor the critical care of patients by determining changes in pO$_2$, pH and perfusion. In such a role, spectrometer of the invention is conveniently adapted to fit around a finger, arm or ear, such as illustrated in FIG. 15.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

Having described the invention, what is claimed as new and secured by Letters Patent is:

1. A method for determining oxygen tension in a biological system, comprising the steps of introducing a physiologically acceptable paramagnetic material to a surface of the biological system, said paramagnetic material having electron paramagnetic resonance spectra responsive to the presence of oxygen, protecting the material from sources of oxygen that are outside of the biological system, and determining the oxygen tension from the electron paramagnetic resonance spectra of the material.

2. A method according to claim 1, wherein the step of protecting the material comprises the step of covering the material with a gas impermeable seal.

3. A method according to claim 2, further comprising the step of sealing the seal to the surface with a substantially gas impermeable grease, the grease being disposed between the seal and the surface.

4. A method according to claim 1, further comprising the step of forming the material into a paramagnetic probe having a disc-like shape.

5. A method according to claim 1, wherein the paramagnetic material is selected from the group consisting essentially of carbonaceous materials including India ink, carbon black, coals, and chars.

6. A method according to claim 1, wherein the paramagnetic material is selected from the group consisting essentially of lithium phthalocyanine, India Ink, carbon black and coal.

7. A method according to claim 1, further comprising the step of utilizing human skin as the biological system.

8. A method for determining oxygen tension in a biological system, comprising the steps of enclosing a paramagnetic material within an inert carrier, said paramagnetic material having electron paramagnetic resonance spectra responsive to the presence of oxygen, introducing the carrier to within the biological system, and determining the oxygen tension of the biological system from the electron paramagnetic resonance spectra of the material within the carrier, wherein the material is disposed within the carrier during the step of determining.

9. A method according to claim 8, wherein the inert carrier comprises a needle, and further comprising the step of connecting a removal member to the needle and so that the removal member extends from the needle to a position exterior to the biological system, whereby the removal member facilitates removal of the needle from the system.

10. A method according to claim 8, further comprising protecting the biological system from material toxicity by utilizing a carrier that is impermeable to the material.

11. A method according to claim 8, further comprising utilizing a cylindrical disc as the carrier.

* * * * *